(12) United States Patent
Brunnett et al.

(10) Patent No.: US 7,488,322 B2
(45) Date of Patent: Feb. 10, 2009

(54) HIGH SPEED SURGICAL CUTTING INSTRUMENT

(75) Inventors: William Charles Brunnett, Jacksonville, FL (US); Dana A. Oliver, Jacksonville, FL (US); Cecil O. Lewis, Jacksonville, FL (US); Kenneth M. Adams, Jacksonville, FL (US)

(73) Assignee: Medtronic, Inc., Minneapolis, MN (US)

( * ) Notice: Subject to any disclaimer, the term of this patent is extended or adjusted under 35 U.S.C. 154(b) by 550 days.

(21) Appl. No.: 10/776,835

(22) Filed: Feb. 11, 2004

(65) Prior Publication Data

US 2005/0177168 A1    Aug. 11, 2005

(51) Int. Cl.
*A61B 17/32* (2006.01)
(52) U.S. Cl. ............................................. 606/79
(58) Field of Classification Search .............. 606/79, 606/80, 84, 85, 170, 180; 433/104; 384/100
See application file for complete search history.

(56) References Cited

U.S. PATENT DOCUMENTS

| | | | |
|---|---|---|---|
| 2,419,045 | A | 4/1947 | Whittaker |
| 4,811,736 | A | 3/1989 | Griggs et al. |
| 5,222,956 | A | 6/1993 | Waldron |
| 5,405,348 | A | 4/1995 | Anspach, Jr. et al. |
| 5,976,165 | A | 11/1999 | Ball et al. |
| 6,033,408 | A | 3/2000 | Gage et al. |
| 2003/0063823 | A1 | 4/2003 | Del Rio et al. |
| 2005/0177168 | A1 | 8/2005 | Brunnett et al. |

FOREIGN PATENT DOCUMENTS

| | | |
|---|---|---|
| EP | 0634146 A2 | 6/1994 |
| EP | 1 155 776 A2 | 11/2001 |
| FR | 1.166.884 | 2/1957 |
| FR | 1.166.884 | 11/1958 |
| JP | 01240615 | 9/1989 |
| JP | 2003021213 | 1/2003 |
| RU | 2 191 898 C2 | 5/2000 |
| WO | WO 03/025102 A1 | 3/2003 |

OTHER PUBLICATIONS

PCT Search Report mailed Dec. 2, 2005 (9 pgs).
B. Dajoux, G. Mazet: "Memento du frottement", Jul. 1994, pp. 22-24 and pp. 36-38.
Bhushan, B: "The Engineering Handbook", 1998, XP002351800; online at www.engnetbase.com; Chap. 21.3-21.5.
F. Kennedy, E. Booser, D: Wilcok: "The Engineering Handbook", 1999, online at www.engnetbase.com; p. 3-129 to 3-133, p. 3-139, 3-141.
PCT Search Report mailed Jan. 16, 2008; 7 pgs.

*Primary Examiner*—Eduardo C Robert
*Assistant Examiner*—David Comstock
(74) *Attorney, Agent, or Firm*—Dicke, Billig & Czaja, PLLC

(57) ABSTRACT

A surgical cutting instrument including an outer tube, inner wire assembly, cutting tip, coupling chuck, and housing. The outer tube includes a lumen extending from a proximal end to a distal end. The inner wire assembly is received within the lumen. Preferably, the outer tube and inner wire assembly form a longitudinally curved segment. The cutting tip is connected to a distal section of the inner wire assembly. The coupling chuck is secured to a proximal section of the inner wire assembly. The housing maintains the outer tube and the coupling chuck. A rotating journal bearing, preferably a rotating-hydrodynamic bearing, is established between the inner wire assembly and the inner surface of the outer tube, allowing nominal rotational speeds of 80,000 RPM. Preferred embodiments of the surgical cutting instrument enhance surgeon visibility, minimize heat build-up, and provide improved stiffness and thermal protection.

132 Claims, 13 Drawing Sheets

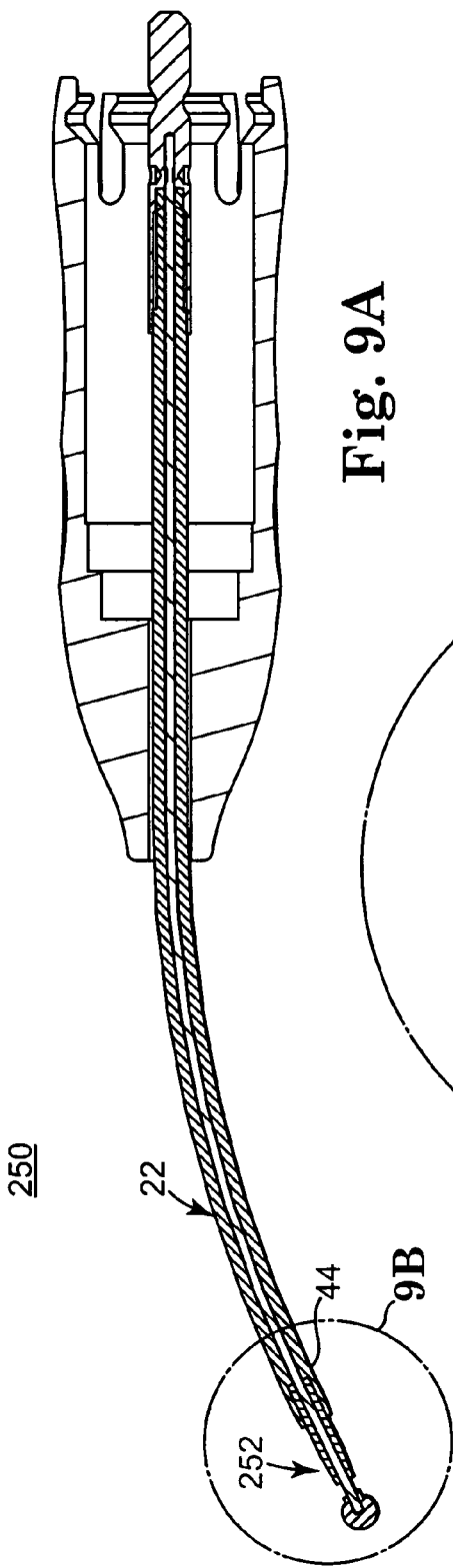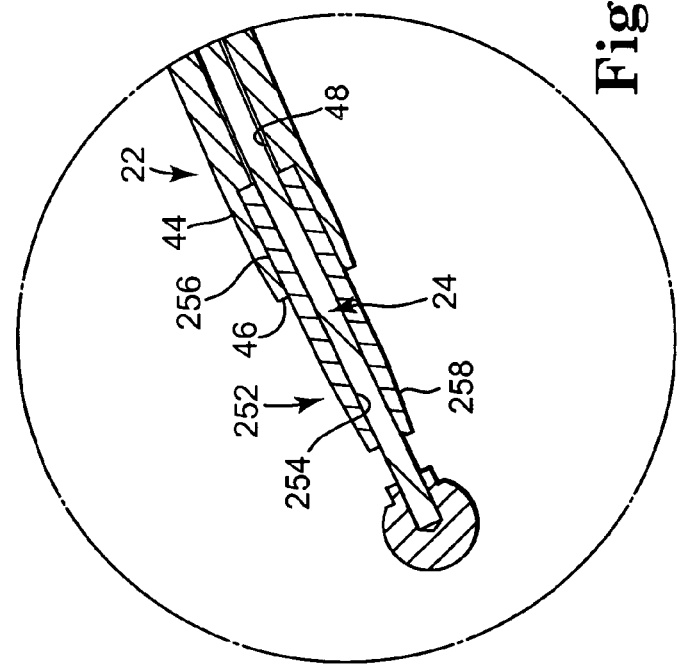
Fig. 9A
Fig. 9B

HIGH SPEED SURGICAL CUTTING INSTRUMENT

BACKGROUND

The present invention relates to a surgical cutting instrument. More particularly, it relates to a surgical cutting instrument, such as a bone-cutting bur, capable of high speed operation and minimal interference with surgical site visibility.

Surgical cutting instruments, such as those incorporating a bur, are commonly used to perform a variety of procedures. For example, many neuro-otological surgical operations entail partial or total removal of bone or other hard tissue via a bur or other cutting tip rotating at high speeds. Exemplary procedures in this field include cochleostomies, removal of acoustic neuroma tumors, removal of the scutum in a tympanoplasty, etc. Numerous other surgical operations have similar bone/hard tissue cutting or removal requirements.

The typical surgical cutting instrument is akin to a drill, including a drill handpiece that rotates a cutting implement. The handpiece houses a motor and a chuck or other adaptor, with the chuck being rotated by the motor under the control of a foot- or finger-operated switch. The cutting implement normally includes a cutting tip (e.g., bur) attached to or formed by a cutter shaft that is otherwise connectable to the handpiece chuck. To provide a clearer view of the surgical site, the cutter shaft is normally elongated to position the cutting tip away from the handle. To this end, if the elongated shaft is unsupported by a separate external sleeve, bur "wobble" inevitably occur and safety concerns are raised by having a large length of exposed shaft rotating at high speeds. If the rotating shaft comes in contact with a nerve or other critical anatomy, serious injuries can occur. Thus, support sleeves are commonly employed.

More particularly, the cutter shaft is disposed within an elongated support sleeve that otherwise extends from a forward end of the housing. The cutter shaft is adapted to be inserted into the sleeve so that a proximal end of the shaft rotatably and releasably engages the chuck. The cutter shaft/support sleeve is commonly referred to as a "bur extender". To provide for high speed concentric rotation of the cutting implement relative to the support sleeve, most surgical cutting instruments employ a ball bearing assembly between the outer support sleeve and the inner cutter shaft at a distal end thereof. While this design can readily operate at speeds in excess of 20,000 RPM, an outer diameter of the support sleeve must be relatively large (on the order of 6 mm) to accommodate the ball bearing assembly. This larger outer dimension, in turn, impairs surgical site visibility, and increases overall costs.

Conventional surgical cutting instrument designs raise additional line-of-sight and handling concerns. In order to support relatively high rotational speeds, most surgical cutting instruments employ a straight bur extender. Unfortunately, with this straight configuration, the support sleeve will often times be in or near the surgeon's line of sight upon desired positioning of the cutting tip at the surgical site, thus impeding the surgeon's view of the surgical site. On a related point, the relatively large outer diameter and/or straight bur extender may affect the surgeon's ability to position the cutting tip at a desired location, especially when the cutting instrument is used in conjunction with a microscope.

One known technique for addressing the line of sight problem described above is to extend the support sleeve/cutter shaft at an angle relative to a central axis of the handpiece. While this technique may improve visibility, handling of the device can be cumbersome as the angular extension initiates immediately adjacent the handpiece, with the bur extender itself remaining straight. With conventional designs, the angled configuration is usually accomplished via beveled gears rotating off-axis from each other. Thus, the angle formed by the bur extender relative to the handpiece axis must be a relatively large distance away from the cutting tip due to the need for the chuck mechanism to be on the same axis as the rotating cutting tip. As a result, only a slight lateral off-set between the cutting tip and the handpiece axis can be achieved, thus minimizing the effect on visibility issues.

In light of the above, it would be desirable to locate the angle or bend away from the handpiece, closer to the cutting tip, such as with a curved bur extender. To this end, one attempt at providing a surgical cutting instrument having a curved bur extender is described in U.S. Pat. No. 4,811,736. While highly viable, this design is potentially limited in the available rotational or cutting speed. In particular, the construction and material selection for the support sleeve and cutter shaft may limit the maximum, viable operational speed to less than 20,000 RPM. This potential limitation may be due in part to the bearing design utilized with the cutting instrument. In particular, U.S. Pat. No. 4,811,736 describes a plastic sleeve bearing 52 disposed within a distal end of an outer support sleeve 33. A cylindrical journal 42 component of the cutting implement (or "bur assembly") is mounted within, and rotates relative to, this plastic sleeve bearing 52. Unfortunately, the additional plastic sleeve bearing 52 component may give rise to failures at high speeds due to excessive heat. Further, an overall diameter of the outer support sleeve 33 must be large enough to accommodate the separate sleeve bearing 52, thus negatively affecting visibility during use. Commercial applications of the teachings of U.S. Pat. No. 4,811,736, such as a drill instrument available from Medtronic-Xomed of Jacksonville, Fla., under the tradename "Skeeter," are not highly stiff.

The above-described surgical cutting instruments often times require additional steps to complete many surgical procedures. For example, a mastoidectomy entails exposing the mastoid periosteum and then carefully drilling/removing the mastoid bone using a cutting/burring instrument and microscope. With a conventional bur extender that is angled relative to the handpiece, but is otherwise straight and employs a ball bearing assembly between a relatively large diameter outer support tube and the cutter shaft, it is highly difficult for the surgeon to visually see the bur cutting tip against the mastoid bone. As such, drilling of the mastoid bone entails first briefly contacting the rotating bur tip against the mastoid bone at an estimated optimal position, and then retracting the bur tip. Once retracted, the surgeon visually determines whether the bur tip was optimally positioned relative to the mastoid bone. If so, the bur tip is returned to the previous point of contact and drilling is commenced, with periodic stoppages to allow the surgeon to visually confirm that the procedure is proceeding as desired. If the initial contact point is less than optimal, the bur tip is repositioned relative to the mastoid bone, and the process repeated. Conversely, with a surgical cutting instrument akin to that described in U.S. Pat. No. 4,811,736, the inherent rotational speed limitations require use of several, differently sized burs. For example, a first, relatively large diameter bur (on the order of 6-7 mm) is initially used to de-bulk a portion of the mastoid bone. Subsequently, a second, smaller diameter bur (on the order of 4-5 mm) is used to remove an additional portion of the mastoid bone. Once visualization of the target site is overtly impaired by this second bur, a third, even smaller diameter bur (on the order of 2 mm) is employed to complete the procedure.

Surgical cutting instruments continue to be important tools for a multitude of surgical procedures. Unfortunately, prior art surgical cutting instruments are characterized as either high speed with poor visibility or lower speed with improved visibility. Therefore, a need exists for a surgical cutting instrument designed for long-term, high-speed operation with minimal impact on user visibility, minimized heat build-up, and improved stiffness.

SUMMARY

One aspect of the present invention relates to a surgical cutting instrument for use with a motor having a drive mechanism. The surgical cutting instrument includes an outer tube, an inner wire assembly, a cutting tip, a coupling chuck, and a housing. The outer tube defines a proximal region terminating at a proximal end, a distal region terminating at a distal end, and a lumen extending from the proximal end to the distal end. In this regard, the lumen is defined by an inner surface of the outer tube. The inner wire assembly is received within the lumen of the outer tube. In this regard, the inner wire assembly includes a proximal section and a distal section such that upon final assembly, the proximal section extends proximally from the proximal end of the outer tube. The cutting tip is connected to the distal section of the inner wire assembly such that at least a portion of the cutting tip extends distal the distal end of the outer tube. The cutting tip can assume a variety of forms, but in one embodiment includes a bur. The coupling chuck is secured to the proximal section of the inner wire assembly. To this end, the coupling chuck is adapted for coupling to a drive mechanism of a drill. The housing maintains the proximal region of the outer tube and the coupling chuck. To this end, the housing is adapted for connection to a drill. With the above in mind, a rotating journal bearing is established between an outer surface of the inner wire assembly and the inner surface of the outer tube, with this rotating journal bearing being formed distal the housing upon rotation of the inner wire assembly relative to the outer tube.

Another aspect of the present invention relates to a surgical cutting instrument for use with a motor having a drive mechanism. The surgical cutting instrument includes an outer tube, an inner wire assembly, a grease lubricant, a cutting tip, a coupling chuck, and a housing. The outer tube defines a proximal region terminating at a proximal end, a distal region terminating at a distal end, and a lumen extending from the proximal end to the distal end. In this regard, the lumen is defined by an inner surface of the outer tube. The inner wire assembly is received within the lumen of the outer tube. In this regard, the inner wire assembly includes a proximal section and a distal section such that upon final assembly, the proximal section extends proximally from the proximal end of the outer tube. The grease lubricant is disposed between the outer tube and the inner wire assembly, and exhibits a dynamic viscosity of not less than 100 mm$^2$/s at 40° C. The cutting tip is connected to the distal section of the inner wire assembly such that at least a portion of the cutting tip extends distal the distal end of the outer tube. The cutting tip can assume a variety of forms, but in one embodiment includes a bur. The coupling chuck is secured to the proximal section of the inner wire assembly. To this end, the coupling chuck is adapted for coupling to a drive mechanism of a motor. The housing maintains the proximal region of the outer tube and the coupling chuck. To this end, the housing is adapted for connection to a motor. With the above in mind, a hydrodynamic, rotating journal bearing is established between an outer surface of the inner wire assembly and the inner surface of the outer tube, with this journal bearing being formed distal the housing upon rotation of the inner wire assembly relative to the outer tube.

Another aspect of the present invention relates to a surgical cutting instrument for use with a motor having a drive mechanism. The surgical cutting instrument includes an outer tube, an inner wire assembly, a cutting tip, a coupling chuck, and a housing. The outer tube defines a proximal region terminating at a proximal end, a distal region terminating at a distal end, and a lumen extending from the proximal end to the distal end. In this regard, the lumen is defined by an inner surface of the outer tube. The inner wire assembly is received within the lumen of the outer tube. In this regard, the inner wire assembly includes a proximal section and a distal section such that upon final assembly, the proximal section extends proximally from the proximal end of the outer tube. The inner wire assembly is formed of a material exhibiting a fatigue strength of at least 75 Kpsi. The cutting tip is connected to the distal section of the inner wire assembly such that at least a portion of the cutting tip extends distal the distal end of the outer tube. The cutting tip can assume a variety of forms, but in one embodiment includes a bur. The coupling chuck is secured to the proximal section of the inner wire assembly. To this end, the coupling chuck is adapted for coupling to a drive mechanism of a motor. The housing maintains the proximal region of the outer tube and the coupling chuck. To this end, the housing is adapted for connection to a motor. With the above in mind, a journal bearing is established between an outer surface of the inner wire assembly and the inner surface of the outer tube, with this journal bearing being formed distal the housing upon rotation of the inner wire assembly relative to the outer tube.

Another aspect of the present invention relates to a surgical cutting instrument for use with a motor having a drive mechanism. The surgical cutting instrument includes an outer tube, an inner wire assembly, a cutting tip, a coupling chuck, and a housing. The outer tube defines a proximal region terminating at a proximal end, a distal region terminating at a distal end, and a lumen extending from the proximal end to the distal end. In this regard, the lumen is defined by an inner surface of the outer wire. The inner wire assembly is received within the lumen of the outer tube. In this regard, the inner wire assembly includes a proximal section and a distal section such that upon final assembly, the proximal section extends proximally from the proximal end of the outer tube. The inner wire assembly is characterized by a Rockwell Hardness of not less than 50 HRC, achieved for example by applying a hardened material coating to the inner wire assembly. The cutting tip is connected to the distal section of the inner wire assembly such that at least a portion of the cutting tip extends distal the distal end of the outer tube. The cutting tip can assume a variety of forms, but in one embodiment includes a bur. The coupling chuck is secured to the proximal section of the inner wire assembly. To this end, the coupling chuck is adapted for coupling to a drive mechanism of a motor. The housing maintains the proximal region of the outer tube and the coupling chuck. To this end, the housing is adapted for connection to a drill motor. With the above in mind, a journal bearing is established between an outer surface of the inner wire assembly and the inner surface of the outer tube, with this journal bearing being formed distal the housing upon rotation of the inner wire assembly relative to the outer tube.

Another aspect of the present invention relates to a surgical cutting instrument for use with a motor having a drive mechanism. The surgical cutting instrument includes an outer tube, an inner wire assembly, a cutting tip, a coupling chuck, and a housing. The outer tube defines a proximal region terminating at a proximal end, a distal region terminating at a distal end, and a lumen extending from the proximal end to the distal end. In this regard, the lumen is defined by an inner surface of the outer tube, with the inner surface exhibiting a surface roughness of not more than 20 μinch RMS. The inner wire assembly is received within the lumen of the outer tube. In this regard, the inner wire assembly includes a proximal section and a distal section such that upon final assembly, the proximal section extends proximally from the proximal end of the outer tube. The cutting tip is connected to the distal section of the inner wire assembly such that at least a portion of the cutting tip extends distal the distal end of the outer tube. The cutting tip can assume a variety of forms, but in one embodiment includes a bur. The coupling chuck is secured to the proximal section of the inner wire assembly. To this end, the coupling chuck is adapted for coupling to a drive mechanism of a motor. The housing maintains the proximal region of the outer tube and the coupling chuck. To this end, the housing is adapted for connection to a motor. With the above in mind, a journal bearing is established between an outer surface of the inner wire assembly and the inner surface of the outer tube, with this journal bearing being formed distal the housing upon rotation of the inner wire assembly relative to the outer tube.

Another aspect of the present invention relates to a surgical cutting instrument for use with a motor having a drive mechanism. The surgical cutting instrument includes an outer tube, an inner wire assembly, a cutting tip, a coupling chuck, and a housing. The outer tube defines a proximal region terminating at a proximal end, a distal region terminating at a distal end, and a lumen extending from the proximal end to the distal end. In this regard, the lumen is defined by an inner surface of the outer tube. The inner wire assembly is received within the lumen of the outer tube. In this regard, the inner wire assembly includes a proximal section and a distal section such that upon final assembly, the proximal section extends proximally from the proximal end of the outer tube. The cutting tip is connected to the distal section of the inner wire assembly such that at least a portion of the cutting tip extends distal the distal end of the outer tube. The cutting tip can assume a variety of forms, but in one embodiment includes a bur. The coupling chuck is secured to the proximal section of the inner wire assembly. To this end, the coupling chuck is adapted for coupling to a drive mechanism of a motor. The housing maintains the proximal region of the outer tube and the coupling chuck. To this end, the housing is adapted for connection to a motor. Upon final assembly, at least a portion of the outer tube distal the housing has a maximum diameter of not more than 2 mm. With the above in mind, a journal bearing is established between an outer surface of the inner wire assembly and the inner surface of the outer tube, with this journal bearing being formed distal the housing upon rotation of the inner wire assembly relative to the outer tube. The instrument is configured to allow inner wire assembly rotational speeds of 80,000 RPM.

Another aspect of the present invention relates to a surgical cutting instrument for use with a motor having a drive mechanism. The surgical cutting instrument includes an outer tube, an inner wire assembly, a cutting tip, a coupling chuck, and a housing. The outer tube defines a proximal region terminating at a proximal end, a distal region terminating at a distal end, and a lumen extending from the proximal end to the distal end. In this regard, the lumen is defined by an inner surface of the outer tube. The inner wire assembly is received within the lumen of the outer tube. In this regard, the inner wire assembly includes a proximal section and a distal section such that upon final assembly, the proximal section extends proximally from the proximal end of the outer tube. The cutting tip is connected to the distal section of the inner wire assembly such that at least a portion of the cutting tip extends distal the distal end of the outer tube. The cutting tip can assume a variety of forms, but in one embodiment includes a bur. The coupling chuck is secured to the proximal section of the inner wire assembly. To this end, the coupling chuck is adapted for coupling to a drive mechanism of a motor. The housing maintains the proximal region of the outer tube and the coupling chuck. To this end, the housing is adapted for connection to a motor. Relative to a distal point of interface between the outer tube and the housing, the outer tube has a stiffness of not less than 15 lbf/inch measured at the distal end of the outer tube. With the above in mind, a journal bearing is established between an outer surface of the inner wire assembly and the inner surface of the outer tube, with this journal bearing being formed distal the housing upon rotation of the inner wire assembly relative to the outer tube.

Another aspect of the present invention relates to a surgical cutting instrument for use with a motor having a drive mechanism. The surgical cutting instrument includes an outer tube, an inner wire assembly, a grease lubricant, a cutting tip, a coupling chuck, and a housing. The outer tube defines a proximal region terminating at a proximal end, a distal region terminating at a distal end, and a lumen extending from the proximal end to the distal end. In this regard, the lumen is defined by an inner surface of the outer tube with this inner surface having a surface roughness of not greater than 20 μinch. The inner wire assembly is received within the lumen of the outer tube. In this regard, the inner wire assembly includes a proximal section and a distal section such that upon final assembly, the proximal section extends proximally from the proximal end of the outer tube. The inner wire assembly exhibits a fatigue strength of at least 75 Kpsi and a hardness of not less that 50 HRC. The grease lubricant is disposed between the outer tube and inner wire assembly, and has a dynamic viscosity of not less than 100 mm$^2$/s at 40° C. The cutting tip is connected to the distal section of the inner wire assembly such that at least a portion of the cutting tip extends distal the distal end of the outer tube. The cutting tip can assume a variety of forms, but in one embodiment includes a bur. The coupling chuck is secured to the proximal section of the inner wire assembly. To this end, the coupling chuck is adapted for coupling to a drive mechanism of a motor. The housing maintains the proximal region of the outer tube and the coupling chuck. To this end, the housing is adapted for connection to a motor. Upon final assembly, at least a portion of the outer tube distal the housing has a maximum outer diameter of not more than 2 mm, and a stiffness of not less than 15 lbf/inch at the distal end relative to a distal point of interface between the outer tube and the housing. With the above in mind, a rotating, hydrodynamic journal bearing is established between an outer surface of the inner wire assembly and the inner surface of the outer tube, with this journal bearing being formed distal the housing upon rotation of the inner wire assembly relative to the outer tube. The above assembly allows for an inner wire assembly speed of 80,000 RPM.

Another aspect of the present invention relates to a method of performing a surgical drilling procedure on tissue at a target site of a patient. The method includes first providing a surgical cutting instrument. The cutting instrument has an outer tube, an inner wire assembly, and a cutting tip. The inner wire assembly is rotatably disposed within the outer tube that otherwise defines a curved segment. The cutting tip is connected to the inner wire assembly, positioned distal a distal end of the outer tube. Tissue at the target site is exposed. The surgical instrument is deployed such that the cutting tip is against the tissue. Finally, the inner wire assembly is rotated at speeds in excess of 50,000 RPM such that the cutting tip removes contacted tissue.

BRIEF DESCRIPTION OF THE DRAWINGS

FIG. 9A is a cross-sectional view of another alternative embodiment surgical cutting instrument in accordance with the present invention including a sealing tip;

FIG. 9B is an enlarged view of a portion of the instrument of FIG. 9A;

DETAILED DESCRIPTION

Figure 1:
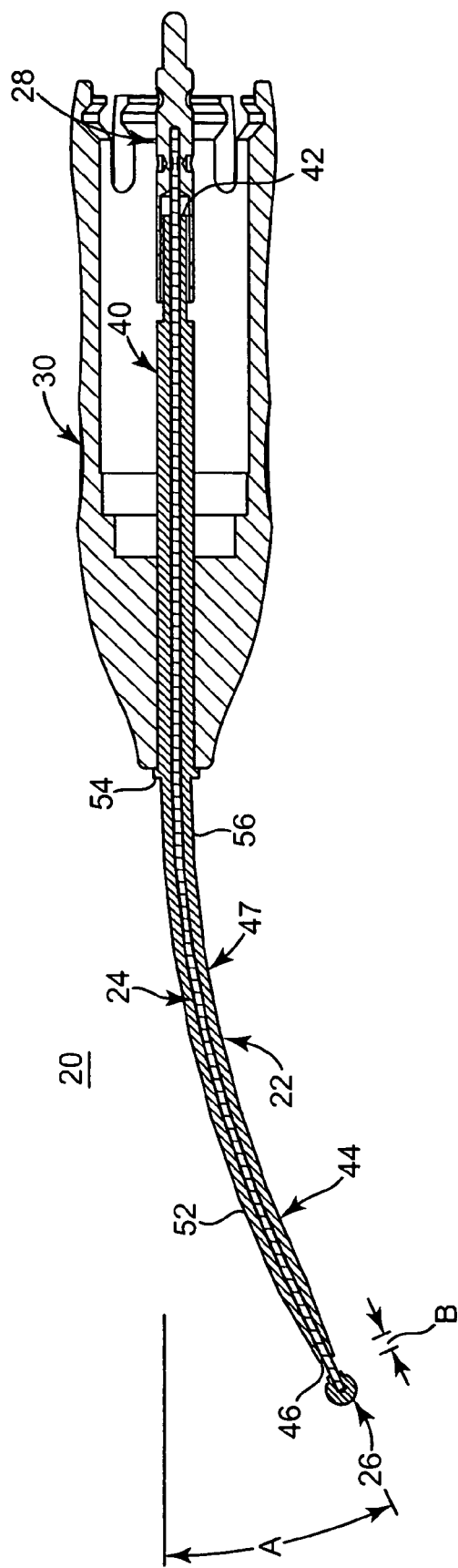
FIG. 1 is a cross-sectional view of a surgical cutting instrument in accordance with the present invention.
Figure 2:
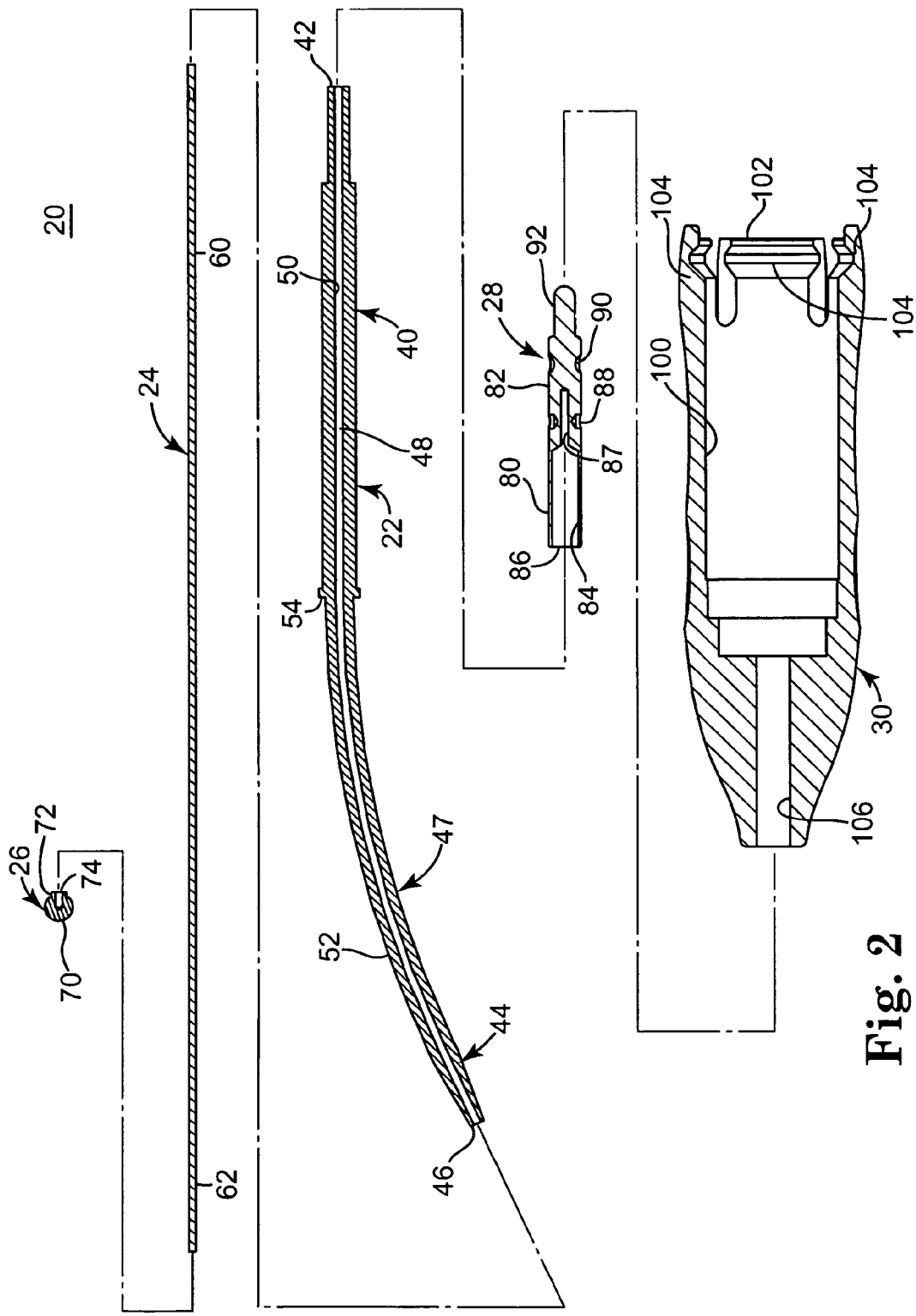
FIG. 2 is an exploded view of the surgical cutting instrument of FIG. 1.

One embodiment of a surgical cutting instrument 20 in accordance with the present invention is shown in FIGS. 1 and 2. The surgical cutting instrument 20 includes an outer support tube 22, an inner wire assembly 24, a cutting tip 26, a coupling chuck 28, and a housing 30. The components 22-30 are described in greater detail below. In general terms, however, the inner wire assembly 24 is coaxially disposed within the outer tube 22. The cutting tip 26 is connected to and extends distally from the inner wire assembly 24. The coupling chuck 28 is secured to the inner wire assembly 24 and is adapted for connection to a drive mechanism (not shown) of a motor (not shown). The housing 30 maintains the outer tube 22 and the coupling chuck 28, and is also adapted for connection to a motor. With this configuration, a bearing is established between the inner wire assembly 24 and the outer tube 22 upon rotation of the inner wire assembly 24 relative to the outer tube 22. As described in greater detail below, the instrument 20 and components thereof provide one or more features that facilitate extremely high rotational speeds (on the order of 80,000 RPM) with the outer tube 22, and thus the inner wire assembly 24, defining one or more curved segments where desired.

The outer tube 22 is an elongated tubular body, defining a proximal region 40 terminating at a proximal end 42, a distal region 44 terminating at a distal end 46, and an intermediate region 47 between the proximal and distal regions 40, 44. Further, the outer tube 22 defines a lumen 48 extending from the proximal end 42 to the distal end 46. Thus, an inner surface 50 of the outer tube 22 forms the lumen 48.

Figure 3:
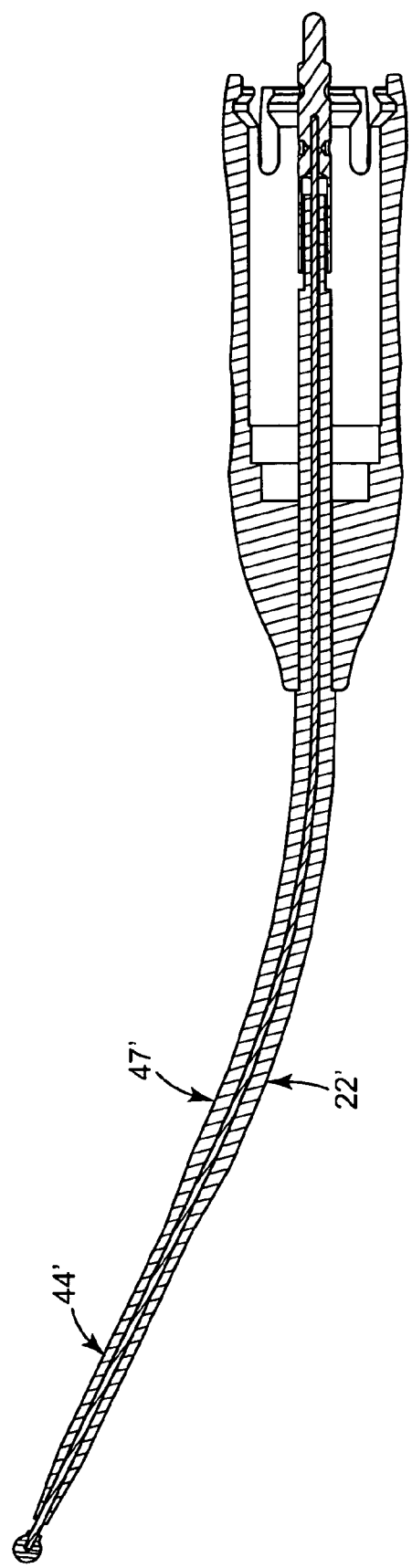
FIG. 3 is a cross-sectional view of an alternative embodiment surgical cutting instrument in accordance with the present invention.

The outer tube 22 can assume a variety of longitudinal shapes, but preferably is of a type allowing for formation of at least one curved segment (referenced generally at 52 in FIG. 1) at or along one or both of the intermediate region 47 and/or the distal region 44. In addition, the outer tube 22 is preferably constructed to facilitate formation of a rotating journal bearing (i.e., frictional sliding journal bearing) relative to the inner wire assembly 24 in conjunction with this preferred curved construction. Finally, the outer tube 22 has a minimal maximum outer diameter, preferably on the order of 2.0 mm, along substantial portions thereof distal the housing 30. As shown in FIG. 1, for example, the intermediate region 47 forms an increased-diameter shoulder 54 that abuts the housing 30, with a remainder of the intermediate region 47 extending distal the housing 30 and having a uniform diameter of about 2.0 mm, including along the curved segment 52 and one or more straight segments 56. In one embodiment, an outer diameter of the outer tube 22 tapers at the distal region 44 to the distal end 46 as shown in FIG. 1. For example, in one embodiment, the outer tube 22 tapers from a diameter of about 2.0 mm to a diameter of about 1.0 mm at the distal end 46. Alternatively, other dimensions can be employed, and the outer tube 22 need not include the distal taper. Depending upon a length of the outer tube 22, portions proximal the distal region 44 can have a slightly larger diameter. For example, and with reference to FIG. 3, where the outer tube 22' has a length of greater than 40 mm, the intermediate region 47' can have an outer diameter on the order of 3.0 mm whereas the distal region 44' has an outer diameter on the order of 2.0 mm and tapers in diameter to the distal end 46'.

Returning to FIG. 1 and as described below, the inner wire assembly 24 is preferably constructed to be thin. This one preferred feature, in combination with the absence of a ball bearing assembly as part of the instrument 20, allows the lumen 48 to have a relatively small diameter, such that even with the preferred, minimized outer diameter described above, the outer tube 22 can have sufficient thickness to provide requisite stiffness when an appropriate material is selected for the outer tube 22. For example, in one embodiment where at least portions of the outer tube 22 have a maximum outer diameter of approximately 2.0 mm, the lumen 48 has a diameter of not more than 1.0 mm, more preferably in the range of 0.25-1.0 mm, more preferably 0.5-0.8 mm, even more preferably 0.55-0.7 mm. Stated otherwise and relative to portions of the outer tube 22 distal the housing having a maximum outer diameter of approximately 2.0 mm, the outer tube 22 has a wall thickness of not less than 0.3 mm, preferably not less than 0.5 mm, even more preferably in the range of 0.6-0.75 mm.

In light of the above, in one embodiment, the outer tube 22 is constructed of a material selected to provide the outer tube 22 with high strength, high stiffness characteristics while satisfying the preferred dimensional and curvature constraints. Stiffness of the outer tube 22 is a function of the material selected for the outer tube 22, as well as an end geometry. As previously described, the outer tube 22 preferably includes the curved segment 52, formation of which can negatively affect a stiffness characteristic of the resultant outer tube 22. Even with a curved configuration (such as with the curved segment 52 defining a radius of curvature of less than 4 inches (10.16 cm), more preferably approximately 3 inches (7.62 cm) or a curve angle A in the range of 20°-30°), however, the outer tube 22 exhibits a stiffness of at least 15 lbf/inch at the distal end 46 relative to the housing 30. Importantly, this preferred stiffness characteristic is achieved with the outer tube 22 having the minimal maximum outer diameter as described above. In one embodiment, it has surprisingly been found that in view of the preferred inner wire assembly 24 (described below) that otherwise facilitates a relatively small outer diameter yet elevated wall thickness for the outer tube 22, the outer tube 22 can be made of conventional surgical instrument materials, such as stainless steel, while satisfying the preferred stiffness and geometry characteristics.

In addition to the preferred dimensions and material selection, in one embodiment, the inner surface 50 of the outer tube 22 is highly polished to facilitate formation of the preferred rotating journal bearing described below. More particularly, it has surprisingly been found that polishing the inner surface 50 of the outer tube 22 to a surface roughness of not greater than 20μ inch, more preferably not greater than 10μ inch, facilitates viability of the surgical cutting instrument 20 incorporating the preferred curvature and dimensional characteristics at high operational speeds. Alternatively, however, in other embodiments, the inner surface 50 need not be highly polished.

The inner wire assembly 24 includes a proximal section 60 and a distal section 62. The inner wire assembly has an overall longitudinal length greater than that of the outer tube 22 such that upon final assembly, the proximal and distal sections 60, 62 extend from the ends 42, 46, respectively, of the outer tube 22.

The inner wire assembly 24 is also preferably constructed to facilitate a rotating journal bearing relative to the outer tube 22 while maintaining structural integrity along a curved axial length. In conjunction with one preferred embodiment in which portions of the outer tube 22 distal the housing 30 have a minimal maximum outer diameter of approximately 2.0 mm, the inner wire assembly 24 is also preferably of a reduced diameter, preferably not more than 0.8 mm, more preferably not more than 0.6 mm, more preferably on the order of 0.5 mm. In one embodiment, the inner wire assembly 24 has a diameter that is 0.05-0.18 mm less than that of the outer tube lumen 48. Further, the inner wire assembly 24 is preferably formed to exhibit high strength and good fatigue characteristics. Fatigue strength is a function of material selection and an end geometry. With the embodiment of FIG. 1 whereby the outer tube 22 imparts a curve onto a longitudinal length of the inner wire assembly 24, the inner wire assembly 24 preferably exhibits a fatigue strength or endurance limit of at least 75 Kpsi. It has surprisingly been found that this preferred fatigue strength characteristic and dimensional limitations can be achieved with an appropriate tool steel material, such as M-series tool steels (molybdenum high speed tool steels), A-series tool steels (medium-alloy air-hardening cold work tool steels), etc. For example, in one embodiment, the inner wire assembly 24 is a homogenous, one-piece wire M2 tool steel. Alternatively, other materials exhibiting the desired durability and fracture resistance can be employed for the inner wire assembly 24, including, for example, other tool steels; 304V high tensile strength drawn wire; other steel wire materials subjected to a roll burnishing process that improves the fatigue strength of the wire by putting the outer surface into a state of compression; other steel wire materials subjected to ultrasonic shot peening or laser shot peening for improving fatigue strength of the wire by putting the outer surface into a state of compression; etc. Even further, other non-steel metals such as iridium, osmium, or ruthenium are acceptable, as are ceramics such as silicon carbide, silicon nitride, boron carbide, titanium carbide, tungsten carbide, etc. Alternatively, however, in other embodiments of the present invention, conventional materials that do not otherwise conform to the above-described strength and stiffness parameters can be employed.

To further enhance wear resistance properties of the inner wire assembly 24, the inner wire assembly 24 is preferably subjected to processing (e.g., heat treated) and/or coated with additional material(s), resulting in a Rockwell Hardness of not less than 50 HRC, more preferably not less than 60 HRC. For example, the selected wire material is preferably coated with a hardened material (not shown in the views of FIGS. 1 and 2) that provides a dense carbon finish to the inner wire assembly 24. In one embodiment, the hardened material coating is a dense carbon (diamond-like coating), coated to a thickness of not more than 0.3 mm. Alternatively, other coating materials can be employed, such as, for example, zirconium nitride, chrome, polytetrafluoroethylene (PTFE) or other fluorocarbon materials, titanium nitride, electroless nickel impregnated with PTFE, etc.

Assembly of the surgical cutting instrument 20 is described in greater detail below. With respect to assembly of the outer tube 22 and the inner wire assembly 24, however, a lubricant (not shown) is preferably provided along a length of the interface between the two components 22, 24 to preferably facilitate formation of a hydrodynamic journal bearing therebetween, whereby the inner wire assembly 24 effectively "floats" relative to the outer tube 22 upon rotation of the inner wire assembly 24, supported by a hydrodynamic effect. With this in mind, the lubricant is preferably a grease lubricant exhibiting a dynamic viscosity of at least 100 mm$^2$/s at 40° C., more preferably in the range of 150-250 mm$^2$/s at 40° C., and is hydrophobic in nature. One acceptable grease lubricant is a synthetic hydrocarbon material thickened with silica available, for example, from Nye Lubricants, Inc., of Fairhaven, Mass., under the trade name Nye NYOGEL® 670. Alternatively, other lubricant materials, such as commercially available greases can be employed.

The cutting tip 26 can assume a variety of forms, and preferably includes a cutting bur 70 and an attachment end 72. The attachment end 72 defines a passage 74 sized to receive the distal section 62 of the inner wire assembly 24. To this end, the cutting tip 26 can be secured to the distal section 62 of the inner wire assembly 24 via a number of known processes such as, for example, welding, brazing, press fitting, thermal shrink fitting, adhesive, etc. Alternatively, the inner wire assembly 24 and the cutting tip 26 can be integrally formed such as by machining the inner wire assembly 24 and the cutting tip 26 from a single piece of stock material. Regardless, the cutting bur 70 can assume a variety of shapes and sizes known in the art (e.g., 2 mm fluted, 1 mm diamond, etc.).

The coupling chuck 28 can assume a variety of forms, but is generally configured to facilitate connection of the drill motor drive mechanism (not shown) to the inner wire assembly 24. As a point of reference, the motor (not shown) and the drive mechanism can assume a variety of forms. The motor can be of a type typically employed with surgical cutting instruments, such as electric, battery powered or pneumatic. Alternatively, any other type of motor or drill drive system can be employed. Similarly, the drive mechanism can be of a type typically employed with surgical cutting instruments that facilitate connection or coupling to the cutting device, such as mechanical connection, a non-contacting magnetical connection, a non-contacting air driven coupling (e.g., an air vane), etc. With this in mind, the coupling chuck 28 of FIGS. 1 and 2 is adapted for use with a mechanical-type drive mechanism, it being understood that the coupling chuck 28 can alternatively be configured in accordance with any other type of drive mechanism.

In one embodiment, the coupling chuck 28 is defined by a distal portion 80 and a proximal portion 82. The distal portion 80 forms a first passage 84 extending from a distal end 86 thereof. The first passage 84 defines a diameter sized to loosely receive the proximal region 40 of the outer tube 22, serving to generally align the outer tube 22 relative to the proximal portion 82. Importantly, the distal portion 80 can rotate freely about the outer tube 22. The proximal portion 82 forms a second passage 87 extending proximally from the first passage 84. The second passage 87 is sized to receive and maintain the proximal section 60 of the inner wire assembly 24. In this regard, the coupling chuck 28 can be further secured to the proximal section 60 of the inner wire assembly 24 by a variety of techniques, such as a crimp 88. In one embodiment, the proximal portion 82 forms a groove 90 and a tang 92 each adapted to facilitate coupling to the drill motor drive shaft. The tang 92 is of a reduced diameter, and serves as a guide surface that promotes rapid, consistent assembly of the drive mechanism to the coupling chuck 28. Once again, however, the coupling chuck 28 can assume a variety of other configurations, as can assembly of the coupling chuck 28 to the outer tube 22 and/or the inner wire assembly 24. For example, the coupling chuck 28 can be an integrally formed part of the inner wire assembly 24.

Similar to the coupling chuck 28, the housing 30 can assume a variety of forms and is generally configured to support the outer tube 22 as well as facilitate attachment of the coupling chuck 28/inner wire assembly 24 to a motor (not shown). To this end, the housing 30 can be insert molded over the outer tube 22. Alternatively, a variety of other assembly techniques, such as gluing, welding, press-fitting, thermal shrink fitting, etc., are equally acceptable. The housing 30 can incorporate a variety of features that facilitate assembly to the motor. In one embodiment, the housing 30 forms a central aperture 100 having an open proximal end 102 defined by a plurality of spaced fingers 104. The central aperture 100 is sized to receive at least a portion of the motor, with the fingers 104 serving to capture the motor within the aperture 100. In addition, or alternatively, the housing 30 can be configured to facilitate attachment to the drill motor via snap fit, threads, interference fit, etc. Further, with the embodiment of FIGS. 1 and 2, the housing 30 defines a passage 106 fluidly connected to the aperture 100. The passage 106 is sized to maintain the outer tube 22, and can be formed during an insert molding procedure.

The surgical cutting instrument 20 is assembled by coaxially disposing the inner wire assembly 24 within the lumen 48 of the outer tube 22. As previously described, in one embodiment a grease lubricant (not shown) is disposed along at least a portion of, preferably an entirety of, an interface between the inner wire assembly 24 and the inner surface 50 of the outer tube 22. The outer tube 22 is assembled to the housing 30 as shown in FIG. 1, with the intermediate region 47 and the distal region 44 extending distal the housing 30. As previously described, the housing 30 can be insert molded over the outer tube 22, with the inner wire assembly 24 then being placed within the lumen 48. Further, the intermediate region 47 can include the shoulder 54 that provides a stop surface for positioning against the housing 30. In one embodiment, various preferred design features of the surgical cutting instrument 20, such as material selections and the resultant bearing, allow for only limited exposure of the inner wire assembly 24 distal the distal end 46 of the outer tube 22, represented at B in FIG. 1. For example, the exposed length B of the inner wire assembly 24 is preferably not greater than 0.1 inch (2.54 mm), more preferably not greater than 0.05 inch (1.3 mm). Regardless, the coupling chuck 28 is secured to the proximal section 60 of the inner wire assembly 24, whereas the cutting tip 26 is attached to the distal section 62.

Figure 4:
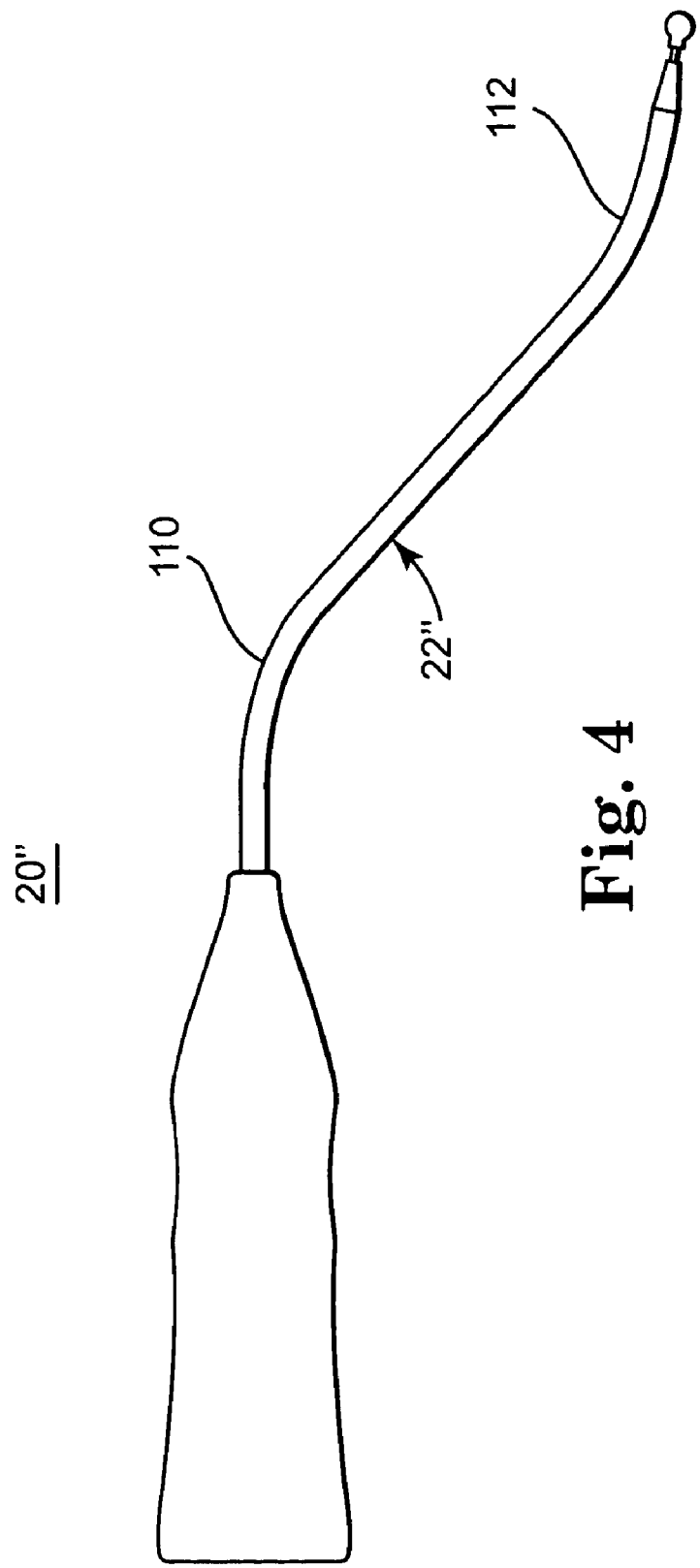
FIG. 4 is a side view of another alterative embodiment surgical cutting instrument in accordance with the present invention.

As previously described, the outer tube 22 preferably includes at least one curved segment 52. Upon placement of the inner wire assembly 24 within the outer tube 22, the inner wire assembly 24 assumes a shape of the outer tube 22, and thus, the curved segment 52. With this in mind, the outer tube 22/inner wire assembly 24 can assume a variety of longitudinal shapes including one or more curved segments (such as the curved segment 52) and one or more straight segments, such as the straight segment 56 shown in FIG. 1. For example, FIG. 4 depicts an alternative embodiment cutting instrument 20" in which the outer tube 22" (and thus the inner wire assembly (not shown)), has two curved segments 110, 112. Alternatively, the outer tube 22, 22" (and thus the inner wire assembly 24) can be straight. Regardless, the dimensions of the straight and/or curved segment(s) are optimized to meet the needs of a particular medical procedure, with the curvature radius (or radii) large enough to ensure that the inner wire assembly 24 (FIG. 1) is deformed within its elastic limit. Once again, with the one preferred embodiment of FIG. 1, the curved segment 52 defines a radius of curvature of approximately 3 inches (7.6 cm), resulting in an off-set angle A of approximately 25°. It has surprisingly been found that the previously described preferred dimensions and material selections for the outer tube 22, the inner wire assembly 24, and the lubricant allow for this one preferred curvature characteristic with high speed, long-term operation as described below.

Returning to FIG. 1, during use, a motor (not shown) is connected to the housing 30, with the drive mechanism (not shown) connected to the coupling chuck 28. The motor is then operated to rotate the coupling chuck 28 and thus the inner wire assembly 24. In one embodiment, rotation of the inner wire assembly 24 relative to the outer tube 22 creates a rotating journal bearing between the inner wire assembly 24 and the inner surface 50 of the outer tube 22 along at least a portion of, preferably an entirety of, a length of the outer tube 22 distal the housing 30. In an even more preferred embodiment, the above-described grease lubricant generates a hydrodynamic journal bearing and/or combination rotating and hydrodynamic journal bearing between the inner wire assembly 24 and the inner surface 50 of the outer tube 22 upon rotation of the inner wire assembly 24. Regardless, the surgical cutting instrument 20 does not include a ball bearing assembly between the outer tube 22 and the inner wire assembly 24.

The surgical cutting instrument 20 of the present invention is capable of maintaining its structural integrity at highly elevated rotational speeds. For example, the surgical cutting instrument 20 can operate at rotational speeds in excess of 50,000 RPM. Further, in one preferred embodiment, where the inner wire assembly 24 is formed of M2 tool steel, the inner surface 50 of the outer tube 22 is highly polished, and a grease lubricant is disposed between the inner wire assembly 24 and the inner surface 50 of the outer tube 22, it has surprisingly been found that the outer tube 22/inner wire assembly 24 can include the curved segment 52 providing an offset angle A of about 25° and a maximum outer diameter of approximately 2.0 mm along a substantial portion thereof while providing a nominal rotational cutting speed of 80,000 RPM with the hydrodynamic-rotating journal bearing having long-term integrity and minimal heat build-up. Thus, the resultant surgical cutting instrument 20 facilitates high-speed surgical cutting procedures with minimal interference to the surgeon's visibility via the small outer diameter, curved nature of the outer tube 22/inner wire assembly 24. The minimal heat generation renders the surgical cutting instrument 20 highly safe for virtually all surgical applications, as does the minimal exposed length B of the inner wire assembly 24. Further, the outer tube 22 is highly stiff, greatly promoting handling and use during a surgical procedure. The above-described performance attributes can be further improved with a hardened material coating (e.g., diamond-like coating) on the inner wire assembly 24. While each of the above-described features (e.g., material selections, processing, lubricant selection) have a synergistic effect in producing a viable, high speed, low profile, curved surgical cutting instrument, variations on one or more of these features can be employed and remain within the scope of the present invention.

Figure 5:
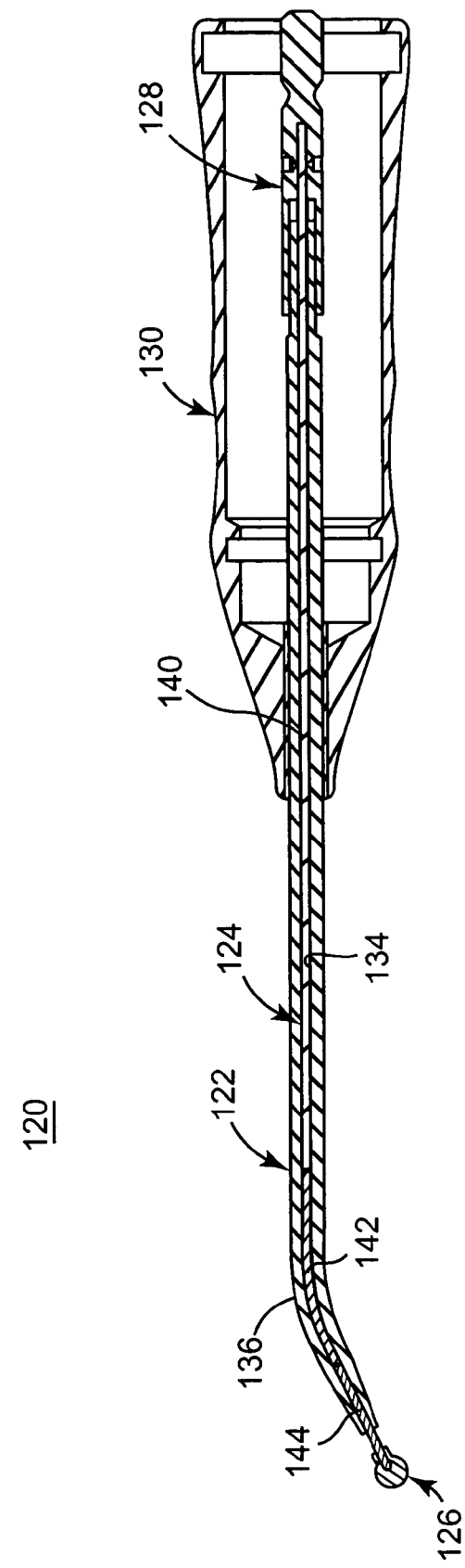
FIG. 5 is a cross-sectional view of another alternative embodiment surgical cutting instrument in accordance with the present invention.

An alternative embodiment surgical cutting instrument 120 is shown in FIG. 5. The surgical cutting instrument 120 is similar to the surgical cutting instrument 20 (FIG. 1) previously described, and includes an outer tube 122, an inner wire assembly 124, a cutting tip 126, a coupling chuck 128, and a housing 130. The outer tube 122, the cutting tip 126, the coupling chuck 128, and the housing 130 are preferably similar to the corresponding components of the cutting instrument 20 (FIG. 1) previously described. The inner wire assembly 124 is described in greater detail below. In general terms, however, the inner wire assembly 124 is coaxially disposed within a lumen 134 defined by the outer tube 122, with the outer tube 122 forming a curved segment 136. Upon final assembly and operation, a rotating journal bearing, preferably a hydrodynamic rotating journal bearing (where a grease lubricant (not shown) is employed), is established between the inner wire assembly 124 and the outer tube 122, with the instrument 120 capable of nominal cutting speeds of 80,000 RPM.

The inner wire assembly 124 includes a proximal section 140, an intermediate section 142, and a distal section 144. The intermediate section 142 is connected at opposite ends thereof to the proximal section 140 and the distal section 144, respectively. In this regard, the proximal and distal sections 140, 144 are high-strength wires or tubes. In a preferred embodiment, the material selected for the proximal section 140 and the distal section 142 is similar to that preferably described with respect to the inner wire assembly 24 (FIG. 1). Conversely, the intermediate section 142 is a flexible, multi-stranded wire coil. The flexible wound coil configuration readily assumes a curved shape, and can be attached to the proximal and distal sections 140, 144 in a variety of fashions such as laser welding or sintering.

The length and location of the intermediate section 142, as well as the proximal and distal sections 140, 144, is a function of a shape of the outer tube 122. For example, as shown in FIG. 5, the inner wire assembly 124 is constructed such that upon final assembly, the intermediate section 142 is disposed within the curved segment 136. Notably, where the outer tube 122 defines two or more curved segments, a corresponding number of intermediate sections/sections of flexible wound coil of wires can be incorporated into the inner wire assembly 124. In another embodiment, one or more of the proximal section 140, intermediate section 142, and/or distal section 144 has a hardened coating applied thereto as previously described. Similarly, in another embodiment, a grease lubricant as previously described is disposed along the inner wire assembly 124/outer tube 122 interface. Regardless, by forming the intermediate section 142 as a flexible wound coil, the intermediate section 142 can maintain a relatively small radius of curvature such that the surgical cutting instrument 120 is conducive to a variety of different surgical procedures.

Figure 6:
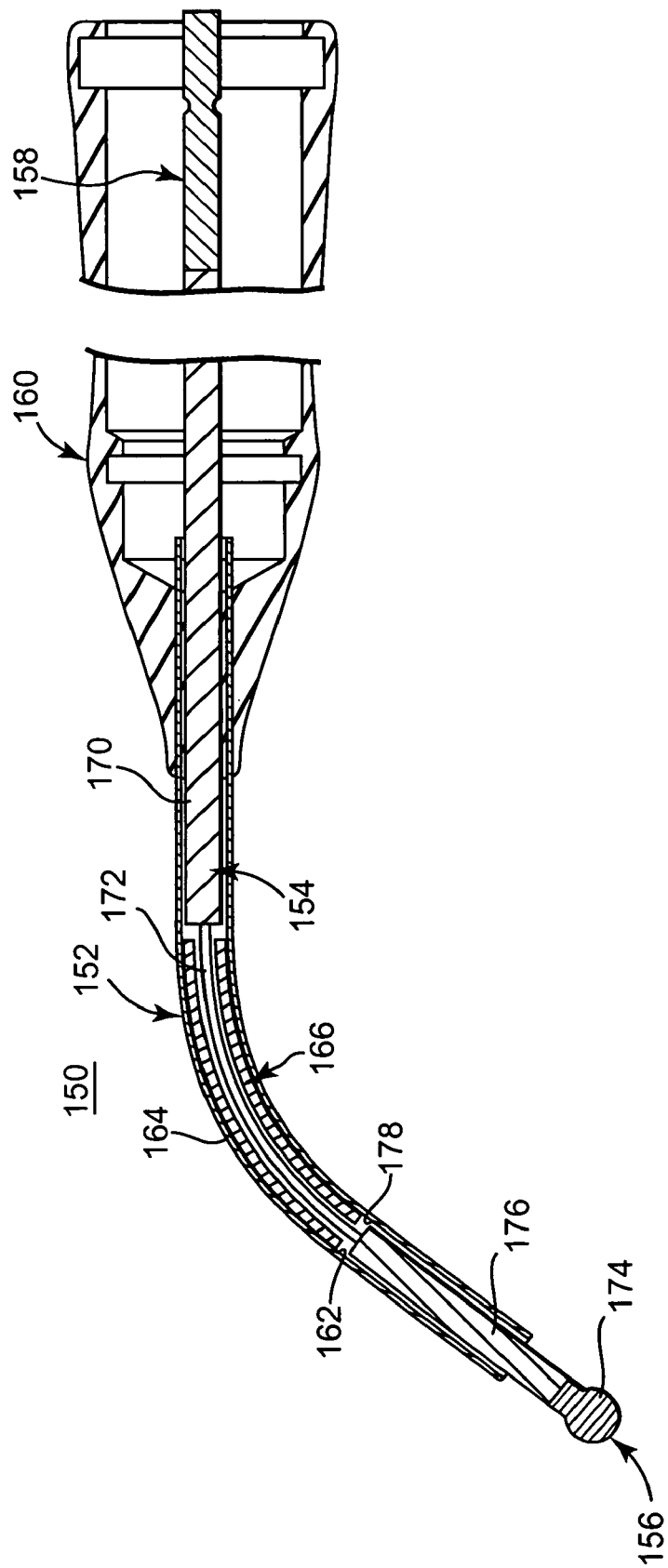
FIG. 6 is a cross-sectional view of another alternative embodiment surgical cutting instrument in accordance with the present invention.

Yet another alternative embodiment surgical cutting instrument 150 is shown in FIG. 6. The cutting instrument 150 is similar to previous embodiments and includes an outer tube 152, an inner wire assembly 154, a cutting tip 156, a coupling chuck 158, and a housing 160. Once again, the inner wire assembly 154 is coaxially disposed within a lumen 162 formed by the outer tube 152 that otherwise includes a curved segment 164. In one preferred embodiment, an intermediate tube 166 is disposed between the outer tube 152 and the inner wire assembly 154 along the curved segment 164.

The outer tube 152 can assume any of the forms previously described with respect to the outer tube 22 (FIG. 1), as can the coupling chuck 158 and the housing 160. The inner wire assembly 154 includes a first section 170 and a second section 172. The first section 172 is a rigid shaft or wire to which the coupling chuck 158 is secured or integrally formed thereby. The second section 172 extends distally from the first section 170 and is a spring wire akin to the inner wire assembly 24 (FIG. 1) previously described. That is to say, the second section 172 can assume any of the forms previously described with respect to the inner wire assembly 24. The first and second sections 170, 172 can be separately formed and fastened together (e.g., laser weld, sintering, etc.), or integrally formed from a single piece of stock material. Regardless, the second section 172 defines a diameter less than that of the first section 170, having an axial length commensurate with an arc length of the curved segment 164 of the outer tube 152.

In one embodiment, the cutting tip 156 includes a cutting bur 174 and a shaft 176. The shaft 176 extends distally from the cutting bur 174 and is attached to the second section 172 of the inner wire assembly 154. Alternatively, the shaft 176 can be formed as part of the inner wire assembly 154, with the cutting bur 174 subsequently attached thereto. For example, the shaft 176 can be of an identical construction as the first section 170. Even further, the cutting tip 156 and the inner wire assembly 154 can be integrally formed. Regardless, the second section 172 has a diameter less than that of the shaft 176.

Notably, the diameter of the second section 172 can be smaller than that of the first section 170 and the shaft 176 because the second section 172 does not need to support the bending load induced by the cutting bur 174. This allows for a reduced radius of the curved segment 164 (along which the second section 172 resides upon final assembly) and reduces the friction load/heat in the curved segment 164.

In one embodiment, the intermediate tube 166 is provided between the second section 172 and the outer tube 152 to support the second section 172 upon rotation of the inner wire assembly 154. In one embodiment, the intermediate tube 166 is formed of a PTFE material; alternatively, other flexible tubing materials can be employed.

During use, the surgical cutting instrument 150 operates in a manner highly similar to previous embodiments. In particular, a motor (not shown) rotates the inner wire assembly 154 relative to the outer tube 152 such that a rotating journal bearing is created between at least a portion of the inner wire assembly 154 and an inner surface 178 of the outer tube 152. In a preferred embodiment, a grease or other lubricant is disposed between portions of the inner wire assembly 154 and the outer tube 152, for example along the first section 170 and/or the shaft 176 of the cutting tip 156 such that at high rotational speeds, a hydrodynamic bearing is established along the outer tube 152. Similar to previous embodiments, then, the surgical cutting instrument 150 is adapted to provide a nominal rotational speed of 80,000 RPM with a low profile, curved outer tube 152 assembly.

Figure 7:
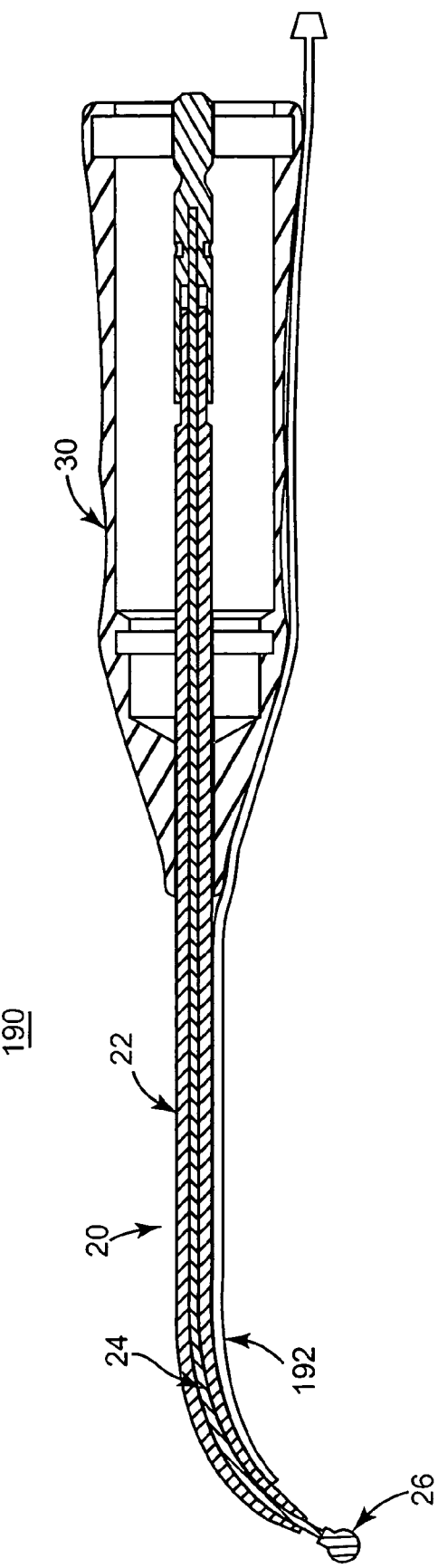
FIG. 7 is a cross-sectional view of another alternative embodiment surgical cutting instrument in accordance with the present invention.

Each of the above-described surgical cutting instruments 20 (FIG. 1), 120 (FIG. 5), and 150 (FIG. 6) can be adapted to provide for target site irrigation. For example, FIG. 7 provides alternative embodiment surgical cutting instrument 190 including the cutting instrument 20 of FIG. 1 along with an irrigation tube 192. The irrigation tube 192 is secured to the housing 30 and the outer tube 22, such as by welding, adhesive, etc. With this configuration, the irrigation tube 192 is fluidly connected at a proximal end thereof to a fluid source (not shown) and thus provides irrigation for the cutting tip 26, thereby eliminating the need for a separate irrigation device. In addition, with fluid flow through the irrigation tube 192, heat is removed from the outer tube 22, thereby facilitating high speed rotation of the inner wire assembly 24 over extended time periods.

Figure 8:
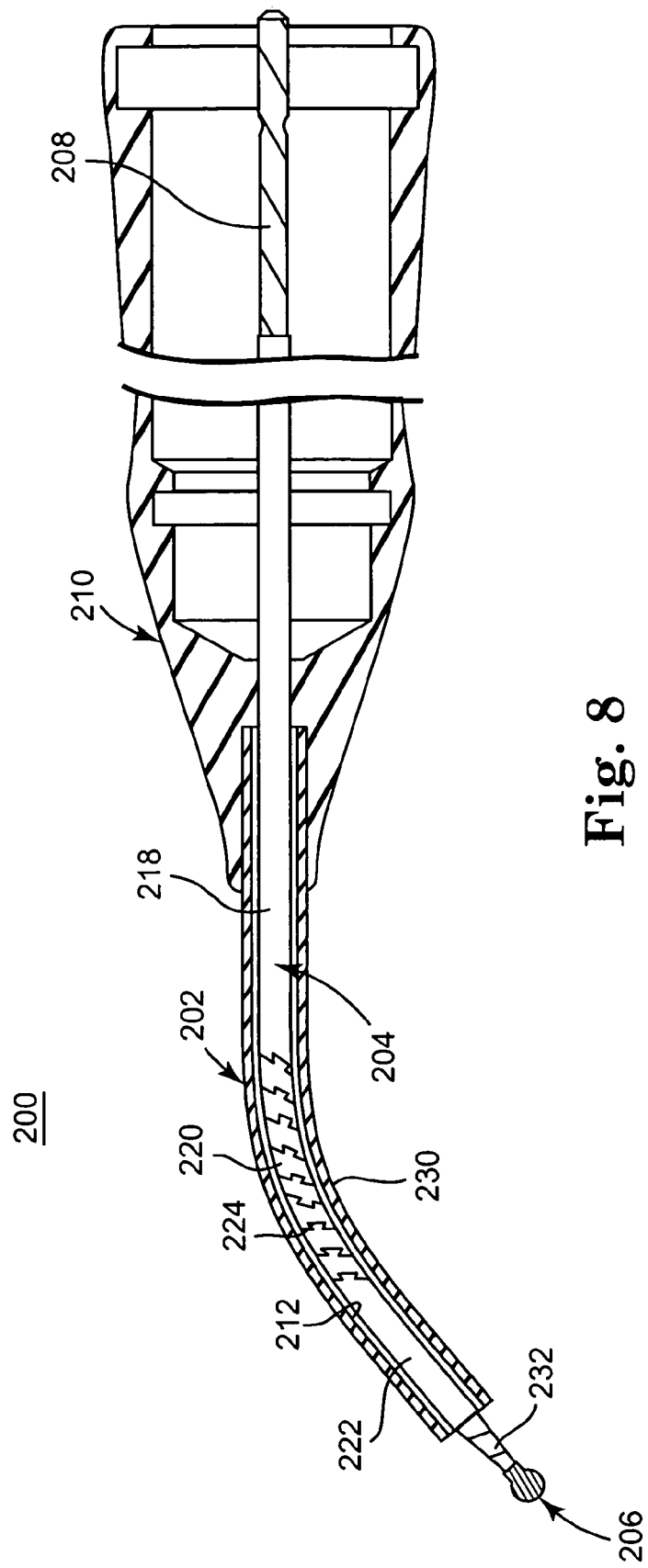
FIG. 8 is a cross-sectional view of another alternative embodiment surgical cutting instrument in accordance with the present invention.

As an alternative to the irrigation tube 192 described above, FIG. 8 depicts yet another alternative embodiment surgical cutting instrument 200 adapted to provide internal irrigation. The surgical cutting instrument 200 includes an outer tube 202, an inner coupling assembly 204, a cutting tip 206, a coupling chuck 208, and a housing 210. The outer tube 202, the coupling chuck 208, and the housing 210 are highly similar to previous embodiments. The inner coupling assembly 204, however, is a tubular member sized to be coaxially received within a lumen 212 of the outer tube 202.

The inner coupling assembly/tubular member 204 includes a proximal section 218, an intermediate section 220, and a distal section 222. A spiral laser cut pattern (referenced generally at 224) is formed along the intermediate section 220 that allows the intermediate section 220 to be flexible, hence to uniformly form and maintain a curved configuration. Thus, upon final assembly, the intermediate section 220 conforms with a shape of a longitudinally curved segment 230 of the outer tube 202. The material selected for the inner coupling assembly 204 is preferably similar to that previously described with respect to the inner wire assembly 24 (FIG. 1). However, an outer diameter of the inner coupling assembly 204 is less than an inner diameter of the outer tube 202/lumen 212. The diametral gap between the inner coupling assembly 204 and the outer tube 202 allows for the delivery of irrigation fluid (not shown) through the outer tube 202. With this construction, the cutting tip 206 preferably includes a shank 232 sized to be received within the inner coupling assembly 204. Alternatively, other techniques for assembling the cutting tip 206 to the inner coupling assembly 204 are equally acceptable.

Additional sealing features can be incorporated into one or more of the surgical cutting instruments described above to minimize flow of material into or out of the outer tube. For example, FIG. 9A is a side, cross-sectional view of an alternative embodiment surgical cutting instrument 250 akin to the surgical cutting instrument 20 of FIG. 1, and further including a sealing tip 252. In particular, the sealing tip 252 is attached to, and extends distally from, the distal region 44 of the outer tube 22, and provides a bearing/sealing surface that more closely approximates an outer diameter of the inner wire assembly 24, thus limiting the possible intake and/or release of material from/to the surgical site.

The sealing tip 252 is formed of a ceramic material, preferably sapphire, and exhibits enhanced hardness and surface finish as compared to the outer tube 22. Thus, the sealing tip 252 has elevated wear characteristics, increasing a life of a bearing formed between the sealing tip 252 and the inner wire assembly 24. Further, ceramic materials can be more readily manufactured to exacting tolerance requirements as compared to steel (as is otherwise preferably used for the outer tube 22) such that an inner lumen 254 of the sealing tip 252 has a diameter less than a diameter of the lumen 48 of the outer tube 22, resulting in a reduced diametrical clearance relative to the inner wire assembly 24. This reduced clearance, in turn, further prevents material from entering and/or exiting the outer tube 22. For example, in one embodiment, the lumen 254 of the sealing tip 252 can be manufactured to provide a diametrical clearance relative to the inner wire assembly 24 in the range of 0.005-0.01 mm.

The sealing tip 252 can be assembled to the outer tube 22 in a variety of fashions. In the one embodiment of FIG. 9B, the outer tube 22 forms an internal aperture or counter-bore 256 at the distal end 46 thereof, having a diameter adapted to receive an outer diameter of the sealing tip 252 via a close slip fit. With this configuration, an adhesive or retaining compound (not shown) secures the sealing tip 252 to the outer tube 22. Regardless, the sealing tip 252 and/or the outer tube 22 are preferably configured to provide a longitudinal interface length of at least 1.5× a diameter of the sealing tip 252 to maintain squareness and straightness. Because the sealing tip 252 is longitudinally straight, an overall length is preferably relatively short when employed with a curved outer tube 22. To provide a sufficient bearing surface, the sealing tip 252 has, in one embodiment, a length in the range of 5.3-7.3 mm, more preferably on the order of 6.35 mm. Finally, the sealing tip 252 has an outer diameter commensurate with, preferably less than, that of the outer tube 252, and preferably forms a distal taper 258. For example, in one embodiment, the sealing tip 252 tapers approximately 0.5-1.5 mm in outer diameter.

Figure 10:
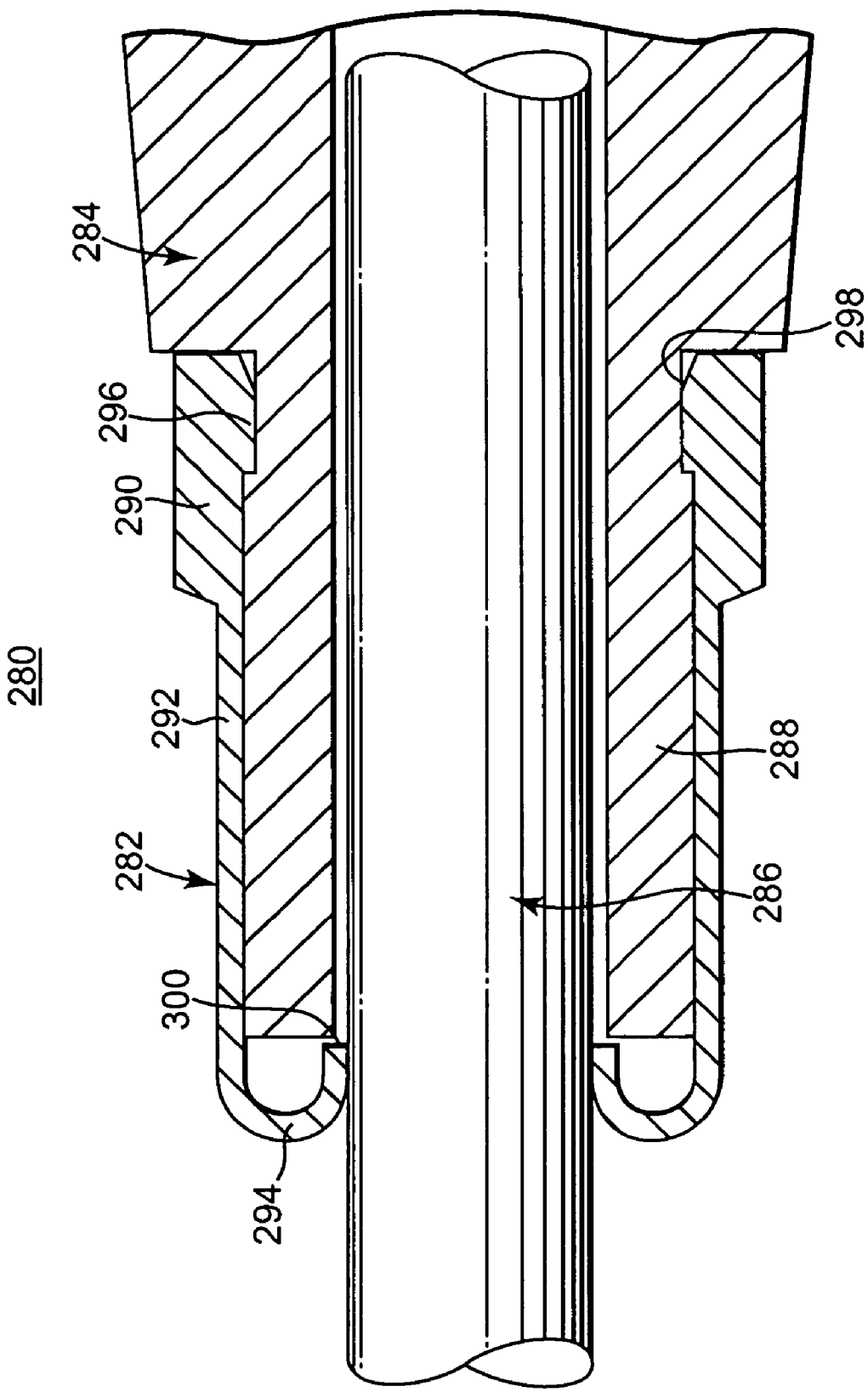
FIG. 10 is an enlarged, cross-sectional view of a portion of another alternative embodiment surgical cutting instrument in accordance with the present invention including a sealing tip.

FIG. 10 illustrates a portion of another alternative embodiment surgical cutting instrument 280 incorporating an alternative sealing tip 282. The surgical cutting instrument 280 can be configured in accordance with any of the previously described embodiments, and includes an outer tube 284 and an inner wire assembly 286 that are, with the one embodiment of FIG. 10, similar to the corresponding elements of the surgical cutting instrument 20 of FIG. 1. For ease of illustration, clearance between the outer tube 284 and the inner wire assembly 286 has been greatly exaggerated in FIG. 10, and the cutting tip 26 (FIG. 1) is not shown. With this in mind, the sealing tip 282 is assembled to a distal region 288 of the outer tube 284, and includes a proximal portion 290, an intermediate portion 292 and a distal portion 294. In one embodiment, the sealing tip 282 is machined from a hardened yet resilient material, such as polytetrafluoroethylene (PTFE), as an integral body. The proximal portion 290 preferably forms a flange 296 sized to be captured within a radial groove 298 formed by the outer tube 284. Alternatively, other techniques for mounting the sealing tip 282 to the outer tube 284 can be employed. The intermediate portion 292 preferably has a reduced outer diameter as compared to the proximal portion 290 to minimize interference with viewing of objects distal the sealing tip 282. Regardless, the distal portion 294 curves or bends inwardly from the intermediate portion 292 to a distal end 300. In particular, the distal end 300 defines a diameter that is less than an outer diameter of the inner wire assembly 286 such that upon final assembly, the distal end 300 is biased against, and is expanded by, the inner wire assembly 286. With this configuration, the distal end 300 effectively forms a seal against the inner wire assembly 286.

Figure 11A:
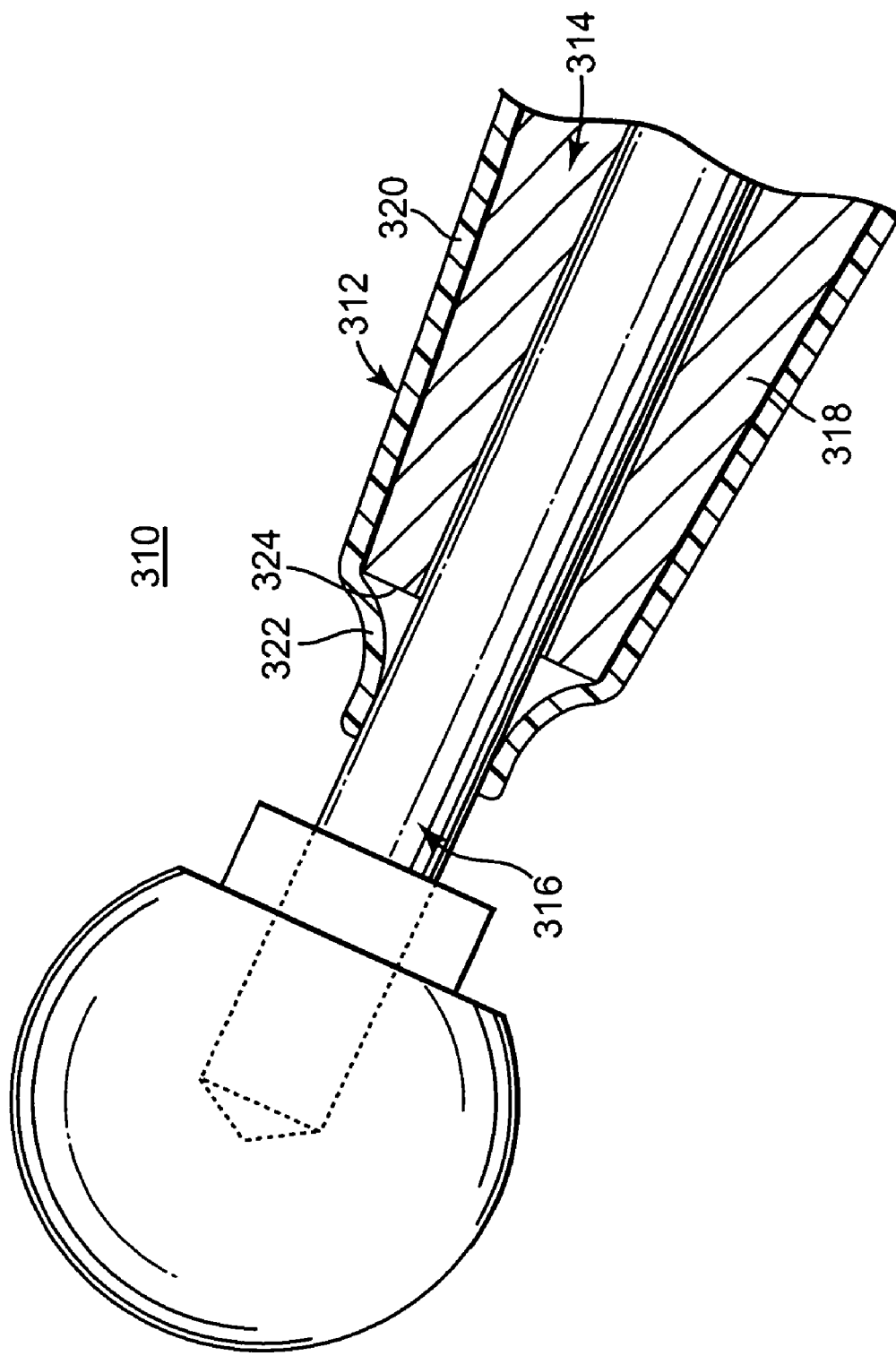
FIG. 11A is an enlarged, partial cross-sectional view of a portion of another alternative embodiment surgical cutting instrument in accordance with the present invention including a sealing tip.

Yet another alternative sealing assembly is illustrated in FIG. 11A. In particular, FIG. 11A depicts a portion of an alternative embodiment surgical cutting instrument 310 including a sealing tip 312. Once again, the sealing tip 312 can be used with any of the cutting instruments previously described and includes, with the one embodiment of FIG. 11A, an outer tube 314 and an inner wire assembly 316 that are similar to that described for the surgical cutting instrument 20 of FIG. 1 (clearance between the outer tube 314 and the inner wire assembly 316 is greatly exaggerated in the view of FIG. 11A). With this in mind, the sealing tip 312 is secured to a distal region 318 of the outer tube 314 and includes a proximal portion 320 and a distal portion 322. In one embodiment, the sealing tip 312 is integrally formed of a shrink tubing material, such as a PTFE shrink tubing. Regardless, the proximal portion 320 is co-axially received over the outer tube 314 such that the distal portion 322 extends distal a distal end 324 of the outer tube 314. The sealing tip 312 is then subjected to a shrinking procedure (e.g., subjected to heat), resulting in the configuration of FIG. 11A. More particularly, the sealing tip 312 is shrunk such that the proximal portion 320 conforms to a corresponding section of the outer tube 314. Further, at least a segment of the distal portion 322 shrinks onto and against the inner wire assembly 316, forming a seal therebetween. In one preferred embodiment, the sealing tip 312 is highly thin (on the order of 0.125 mm) and has a minimal distal extension relative to the distal end 324 of the outer tube 314, on the order of 0.5 mm. Alternatively, other dimensions can be employed.

Figure 11B:
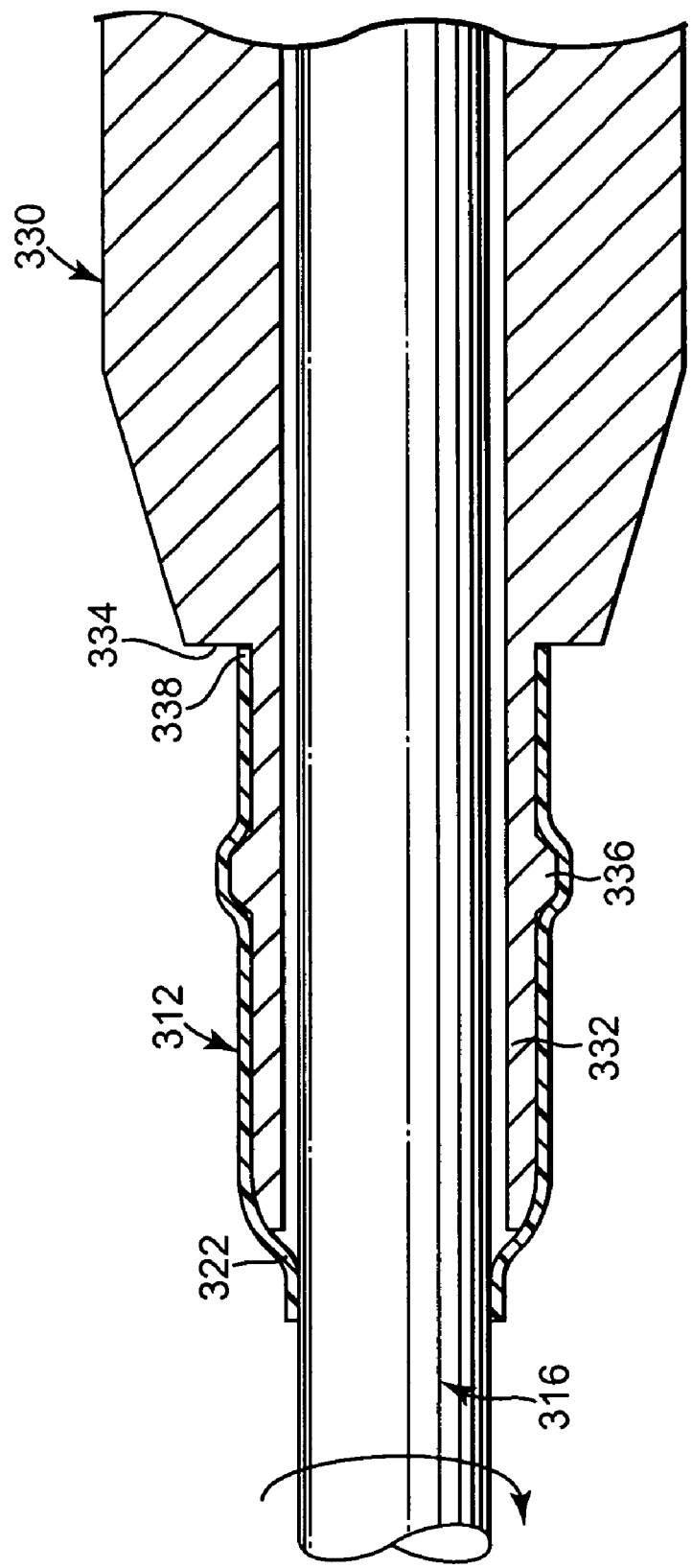
FIG. 11B is an enlarged, partial cross-sectional view of a portion of another alternative embodiment surgical cutting instrument in accordance with the present invention including a sealing tip.

FIG. 11B depicts an alternative technique for mounting of the sealing tip 312. In particular, an alternative outer tube 330 is provided, a distal region 332 of which forms a radial shoulder 334 and a flange 336. The sealing tip 312 is assembled over the distal region 332 of the outer tube 330 such that a proximal end 338 abuts the shoulder 334. The sealing tip 312 is then subjected to a shrinking operation, resulting in the configuration of FIG. 1B. The shoulder 334 ensures that the distal portion 322 of the sealing tip 312 extends distal the outer tube 330 and engages the inner wire assembly 316. Further, the flange 336 effectively locks the sealing tip 312 relative to the outer tube 330 such that the sealing tip 312 will not move longitudinally relative to the outer tube 330.

Figure 12:
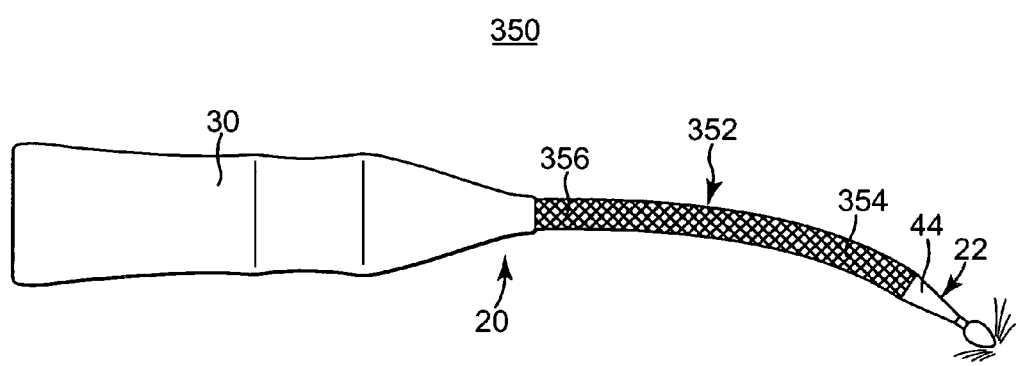
FIG. 12 is side view of another alternative embodiment surgical cutting instrument in accordance with the present invention including a cooling device.

Additional features can be incorporated into one or more of the surgical cutting instruments described above, or embodiments not specifically described, that further minimize heat build-up during continuous, high speed operation. For example, FIG. 12 depicts another alternative embodiment surgical cutting instrument 350 including the cutting instrument 20 of FIG. 1 along with an evaporative cooling sleeve 352. Notably, the evaporative cooling sleeve 352 can be employed with any of the other surgical cutting instrument embodiments described herein. With reference to the one embodiment of FIG. 12, the cooling sleeve 352 is secured over an exterior of the outer tube 22, preferably extending from the housing 30 to the distal region 44. The cooling sleeve 352 is preferably formed of a fabric material such as nylon, silk, polypropylene, polyester, cotton, etc., and is preferably uncoated nylon. Regardless, the cooling sleeve 352 readily conforms to any curved segment(s) defined by the outer tube 22 and can be constructed as a braided tube or a coil of thread wound directly onto the outer tube 22. In one embodiment, opposing ends of the cooling sleeve 352 are secured to the outer tube 22 by clamping or adhesive. The cooling sleeve 352 is constructed to absorb fluids (e.g., bodily fluids at a surgical site, irrigation fluids delivered during a surgical procedure, etc.), preferably wicking the absorbed fluids toward the housing 30. That is to say, as fluids are absorbed at a distal region 354 of the cooling sleeve 352, the so-absorbed fluids will transfer or conduct toward a proximal region 356 until an entirety of the cooling sleeve 352 is saturated. While the cooling sleeve 352 is shown in FIG. 12 as extending along a substantial length of the outer tube 22, in alternative embodiments, the cooling sleeve 352 need not extend to the housing 30. Conversely, the cooling sleeve 352 can alternatively be constructed and sized to encompass an entirety of the outer tube 22.

During use, fluids absorbed by the cooling sleeve 352 will evaporate via heat generated by rotation of the inner wire assembly 24 (FIG. 2) relative to the outer tube 22, serving to cool the outer tube 22. With this construction, as the outer tube 22 conducts more heat, the evaporative process facilitated by the cooling sleeve 352 will become more aggressive, regulating a surface temperature of the outer tube 22 to a relatively consistent level. For example, it has been found that regardless of a temperature of the outer tube 22, the cooling sleeve 352 of the present invention will, in the presence of fluids, cool the outer tube 22 to a substantially nominal temperature (within 10° C.). Regardless, an enhanced cooling effect is provided preferably in conjunction with at least partial removal of fluids from the surgical site.

The surgical cutting instrument of the present invention provides a marked improvement over previous designs. By eliminating a need for a ball bearing assembly in conjunction with preferred material selections and processing techniques, the outer support tube can have an outer diameter significantly less than other available surgical instruments along with optimally located and sized curved section(s), while providing requisite stiffness. Further, the preferred material selections and, where desired, lubricant allows for long-term high-speed rotation (on the order of 80,000 RPM) with minimal instrument wear and heat build-up. Finally, the surgical cutting instrument of the present invention requires a minimal number of components, thus reducing costs and assembly time.

Due to the preferred high speed, curved, low profile features, the surgical cutting instrument of the present invention can be used in a wide variety of applications. One field of possible applications includes numerous neuro-otology procedures, such as cochlear implant, cochleostomy, tympanoplasty, ossicular chain reconstruction, acoustic neuroma surgery (e.g., middle and posterior fossa approaches), drainage of petrous apex cysts, and mastoidectomies, to name but a few. In addition, the surgical cutting instrument of the present invention can be used for a variety of other bodily procedures, such as those relating to sinus surgery, removal of bone spurs on the vertebrae, removal of arthritic bone spurs throughout the body, spinal disc surgery, knee surgery, hip surgery, orthopedic surgical procedures, etc.

For example, the surgical cutting instrument 20 (FIG. 1) can be used to perform a cochleostomy procedure. The primary goals of this surgery are to anchor a receiver-stimulator package in the temporal bone in the skull and to insert an electrode array into the cochlea. In accordance with one embodiment of the present invention, skin behind the ear at which the cochleostomy is to be performed is raised from the skull to expose the temporal bone. A surgical drill is used to remove (debulk) a large portion of the mastoid bone. If desired, upon approaching critical anatomy, a smaller cutting tip is then employed to resect the mastoid bone until the facial recess is reached. Regardless, at this point, the high speed surgical cutting instrument of the present invention, preferably with a curved configuration and including a 2 mm cutting tip, is deployed and operated (i.e., at speeds of at least 50,000 RPM) to resect the bone through the facial recess. This represents a critical part of the procedure because the facial nerve runs along side of the facial recess. To this end, the surgical cutting instrument of the present invention with the curved configuration protects the facial nerve as the outer tube extends into the facial recess, thus minimizing exposure of the facial nerve to the rotating inner wire that might otherwise unexpectedly contact the facial nerve and/or cause thermal damage. Further, the curved, minimal outer diameter preferred features of the surgical cutting instrument of the present invention affords the surgeon vastly improved visibility of the surgical site as compared to conventional cutting devices. After the middle ear cavity is reached, the 2 mm cutting tip can be replaced by a 1.0 mm or 0.5 mm cutting tip for drilling a small hole into the cochlea. Regardless, the improved visibility associated with the surgical cutting instrument of the present invention assists in ensuring that the hole is placed correctly. The electrode array is then inserted into the cochlea and the wound is closed.

The above-described surgical procedure is but one example of a use of the surgical cutting instrument of the present invention. Once again, the surgical cutting instrument facilitates a multitude of other surgeries. In more general terms, and in accordance with one preferred embodiment, the surgical cutting instrument is provided in a curved configuration, deployed against exposed tissue, such as bone, at a target site, and operated at speeds in excess of 50,000 RPM to remove (e.g., cut, drill, resect, etc.) contacted tissue. Although the present invention has been described with reference to preferred embodiments, workers skilled in the art will recognize that changes can be made in form and detail without departing from the spirit and scope of the present invention.

What is claimed is:

1. A surgical cutting instrument for use with a motor having a drive mechanism, the instrument comprising:
   an outer tube defining a first curved segment, a proximal region terminating at a proximal end, a distal region terminating at a distal end, and a lumen extending from the proximal end to the distal end, the lumen being defined by an inner surface of the outer tube;
   an inner wire assembly received within the lumen and comprising a wire, the inner wire assembly including a proximal section and a distal section, wherein the proximal section extends proximally from the proximal end of the outer tube;
   a cutting tip connected to the distal section of the inner wire assembly, wherein at least a portion of the cutting tip extends distal the distal end of the outer tube;
   a coupling chuck secured to the proximal section of the inner wire assembly, wherein the coupling chuck is adapted for connection to a drive mechanism of a motor; and
   a housing maintaining the proximal region of the outer tube and the coupling chuck, the housing being adapted for connection to a motor;
   wherein a rotating journal bearing is established between an outer surface of the inner wire assembly and an entirety of a length of the inner surface of the outer tube distal the housing upon rotation of the inner wire assembly relative to the outer tube;
   wherein upon final assembly, the wire assumes a shape of the first curved segment;
   and further wherein the instrument is configured to allow rotation of the inner wire assembly relative to the outer tube at a speed in excess of 50,000 RPM without failure of the bearing.

2. The instrument of claim 1, wherein the instrument is characterized by the absence of a ball bearing assembly between the outer tube and the inner wire assembly.

3. The instrument of claim 1, further comprising:
   a lubricant disposed between the outer surface of the inner wire assembly and the inner surface of the outer tube;
   wherein upon rotation of the inner wire assembly relative to the outer tube, the lubricant is adapted to create a hydrodynamic effect between the inner wire assembly and the outer tube.

4. The instrument of claim 1, wherein the wire is homogenous.

5. The instrument of claim 4, wherein the wire is a tool steel.

6. The instrument of claim 4, wherein at least a portion of the outer tube distal the housing has a maximum outer diameter of not more than 2 mm.

7. The instrument of claim 4, wherein the wire has an outer diameter of not more than 0.8 mm.

8. The instrument of claim 4, wherein an exposed portion of the wire extends distally from the distal end of the outer tube, and further wherein a length of the exposed portion is not greater than 2.54 mm.

9. The instrument of claim 4, wherein the distal region of the outer tube tapers distally in diameter to the distal end.

10. The instrument of claim 1, further comprising:
    a sealing tip connected to the distal region of the outer tube, at least a portion of the sealing tip defining an inner diameter that is less than a diameter of the lumen of the outer tube.

11. The instrument of claim 10, wherein the sealing tip is a ceramic body.

12. The instrument of claim 10, wherein the sealing tip is a tubular body having a proximal portion and a distal portion, the distal portion defining a relaxed state diameter that is less than a diameter of the inner wire assembly, and further wherein upon final assembly, the distal portion of the sealing tip is forced to an expanded state diameter via contact with the inner wire assembly.

13. The instrument of claim 10, wherein the sealing tip is a tubular body shrunk fit to the outer tube and a portion of the inner wire assembly.

14. The instrument of claim 1, wherein the outer tube further defines a second curved segment apart from the first curved section, and further wherein upon final assembly, the wire assumes a shape of the second curved segment.

15. The instrument of claim 1, further comprising:
    a cooling sleeve disposed over at least a portion of the outer tube.

16. The instrument of claim 1, wherein the inner wire assembly further defines an intermediate section comprised of a flexible, multi-stranded coil of wires, the intermediate section being connected at opposite ends thereof to the proximal and distal sections, respectively.

17. The instrument of claim 16, wherein the proximal and distal sections are wires.

18. The instrument of claim 16, wherein at least a portion of the rotating journal bearing is established between the inner surface of the outer tube and the flexible wound coil of wires.

19. The instrument of claim 16, wherein the outer tube defines a curved segment, and further wherein upon final assembly, the flexible coil of wires assumes a shape of the curved segment.

20. The instrument of claim 1, wherein the inner wire assembly includes a first portion and a second portion, the first portion being a rigid wire and the second portion being a flexible wire, and further wherein the second portion is connected to, and extends distally from, a distal end of the first portion, the cutting tip being connected distal a distal end of the second portion.

21. The instrument of claim 20, wherein the outer tube defines a curved segment, and further wherein upon final assembly, the second portion of the inner wire assembly assumes a shape of the curved segment.

22. The instrument of claim 21, further comprising:
an intermediate tube disposed between the inner surface of the outer tube and an outer surface of the second portion of the inner wire assembly along the curved segment of the outer tube.

23. The instrument of claim 20, wherein the second portion has a diameter less than a diameter of the first portion.

24. The instrument of claim 1, wherein the lumen of the outer tube has a constant diameter in extension from the housing to the distal end.

25. The instrument of claim 1 wherein the coupling chuck includes a first passageway defining a first diameter to receive the proximal end of the outer tube and a second passageway defining a second diameter, smaller than the first diameter, to receive the inner wire assembly.

26. A surgical cutting instrument for use with a motor having a drive mechanism, the instrument comprising:
an outer tube defining a first curved segment, a proximal region terminating at a proximal end, a distal region terminating at a distal end, and a lumen extending from the proximal end to the distal end, the lumen being defined by an inner surface of the outer tube;
an inner wire assembly received within the lumen and comprising a wire, the inner wire assembly including a proximal section and a distal section, wherein the proximal section extends proximally from the proximal end of the outer tube;
a grease lubricant disposed between the inner surface of the outer tube and an outer surface of the inner wire assembly, the grease lubricant exhibiting a dynamic viscosity of not less than 100 mm$^2$/s at 40° C.;
a cutting tip connected to the distal section of the inner wire assembly, wherein at least a portion of the cutting tip extends distal the distal end of the outer tube;
a coupling chuck secured to the proximal section of the inner wire assembly, wherein the coupling chuck is adapted for connection to a drive mechanism of a motor; and
a housing maintaining the proximal region of the outer tube and the coupling chuck, the housing being adapted for connection to a motor;
wherein a hydrodynamic, rotating journal bearing is established by the grease lubricant between an outer surface of at least a portion of the inner wire assembly and the inner surface of the outer tube distal the housing upon rotation of the inner wire assembly relative to the outer tube;
wherein upon final assembly, the wire assumes a shape of the first curved segment;
and further wherein the instrument is configured to allow rotation of the inner wire assembly relative to the outer tube at a speed in excess of 50,000 RPM, without failure of the bearing.

27. The instrument of claim 26, wherein the grease lubricant exhibits a dynamic viscosity in the range of 150-250 mm$^2$/s at 40° C.

28. The instrument of claim 26, wherein the grease lubricant is a synthetic hydrocarbon thickened with silica.

29. The instrument of claim 26, wherein the grease lubricant is hydrophobic.

30. The instrument of claim 26, wherein the instrument is characterized by the absence of a ball bearing assembly between the outer tube and the inner wire assembly.

31. The instrument of claim 26, wherein the wire is homogenous.

32. The instrument of claim 31, wherein the wire is a tool steel.

33. The instrument of claim 31, wherein the hydrodynamic bearing is established along an entirety of a length of the outer tube distal the housing.

34. The instrument of claim 31, wherein at least a portion of the outer tube distal the housing has a maximum outer diameter of not more than 2 mm.

35. The instrument of claim 31, wherein the wire has an outer diameter of not more than 0.8 mm.

36. The instrument of claim 31, wherein an exposed portion of the wire extends distally from the distal end of the outer tube, and further wherein a length of the exposed portion is not greater than 2.54 mm.

37. The instrument of claim 31, wherein the distal region of the outer tube tapers distally in diameter to the distal end.

38. The instrument of claim 26, further comprising:
a sealing tip connected to the distal region of the outer tube, at least a portion of the sealing tip defining an inner diameter that is less than a diameter of the lumen of the outer tube.

39. The instrument of claim 38, wherein the sealing tip is a ceramic body.

40. The instrument of claim 38, wherein the sealing tip is a tubular body having a proximal portion and a distal portion, the distal portion defining a relaxed state diameter that is less than a diameter of the inner wire assembly, and further wherein upon final assembly, the distal portion of the sealing tip is forced to an expanded state diameter via contact with the inner wire assembly.

41. The instrument of claim 39, wherein the sealing tip is a tubular body shrunk fit to the outer tube and a portion of the inner wire assembly.

42. The instrument of claim 26, further comprising:
a cooling sleeve disposed over at least a portion of the outer tube.

43. A surgical cutting instrument for use with a motor having a drive mechanism, the instrument comprising:
an outer tube defining a first curved segment, a proximal region terminating at a proximal end, a distal region terminating at a distal end, and a lumen extending from the proximal end to the distal end, the lumen being defined by an inner surface of the outer tube;
an inner wire assembly received within the lumen and comprising a wire, the inner wire assembly including a proximal section and a distal section, wherein the proximal section extends proximally from the proximal end of the outer tube, and further wherein the inner wire assembly is formed of a material exhibiting a fatigue strength of at least 75 Kpsi;
a cutting tip connected to the distal section of the inner wire assembly, wherein at least a portion of the cutting tip extends distal the distal end of the outer tube;
a coupling chuck secured to the proximal section of the inner wire assembly, wherein the coupling chuck is adapted for connection to a drive mechanism of a motor; and a housing maintaining the proximal region of the outer tube and the coupling chuck, the housing being adapted for connection to a motor;

wherein a bearing is established between an outer surface of at least a portion of the inner wire assembly and at least a portion of the inner surface of the outer tube distal the housing upon rotation of the inner wire assembly relative to the outer tube;

and further wherein upon final assembly, the wire assumes a shape of the first curved segment.

44. The instrument of claim 43, wherein the inner wire assembly is formed of tool steel.

45. The instrument of claim 44, wherein the tool steel is an M-series tool steel.

46. The instrument of claim 45, wherein the tool steel is M2 tool steel.

47. The instrument of claim 43, wherein the outer tube and the inner wire assembly are formed of a metal processed to provide the fatigue strength.

48. The instrument of claim 47, wherein the metal is subjected to a roll burnishing process.

49. The instrument of claim 47, wherein the metal is subjected to one of ultrasonic shot peening and laser shot peening.

50. The instrument of claim 43, wherein the instrument is characterized by the absence of a ball bearing assembly between the outer tube and the inner wire assembly.

51. The instrument of claim 43, wherein a rotating journal bearing is established between an outer surface of the inner wire assembly and the inner surface of the outer tube upon rotation of the inner wire assembly relative to the outer tube.

52. The instrument of claim 43, wherein the wire is homogenous.

53. The instrument of claim 52, wherein the journal bearing is established along an entirety of a length of the outer tube distal the housing.

54. The instrument of claim 52, wherein at least a portion of the outer tube distal the housing has a maximum outer diameter of not more than 2 mm.

55. The instrument of claim 52, wherein the wire has an outer diameter of not more than 0.8 mm.

56. The instrument of claim 52, wherein an exposed portion of the wire extends distally from the distal end of the outer tube, and further wherein a length of the exposed portion is not greater than 2.54 mm.

57. The instrument of claim 52, wherein the distal region of the outer tube tapers distally in diameter to the distal end.

58. The instrument of claim 43, further comprising:
a sealing tip connected to the distal region of the outer tube, at least a portion of the sealing tip defining an inner diameter that is less than a diameter of the lumen of the outer tube.

59. The instrument of claim 58, wherein the sealing tip is a ceramic body.

60. The instrument of claim 58, wherein the sealing tip is a tubular body having a proximal portion and a distal portion, the distal portion defining a relaxed state diameter that is less than a diameter of the inner wire assembly, and further wherein upon final assembly, the distal portion of the sealing tip is forced to an expanded state diameter via contact with the inner wire assembly.

61. The instrument of claim 58, wherein the sealing tip is a tubular body shrunk fit to the outer tube and a portion of the inner wire assembly.

62. The instrument of claim 43, further comprising:
a cooling sleeve disposed over at least a portion of the outer tube.

63. A surgical cutting instrument for use with a motor having a drive mechanism, the instrument comprising:

an outer tube defining a first curved segment, a proximal region terminating at a proximal end, a distal region terminating at a distal end, and a lumen extending from the proximal end to the distal end, the lumen being defined by an inner surface of the outer tube;

an inner wire assembly received within the lumen and comprising a wire, the inner wire assembly including a proximal section and a distal section, wherein the proximal section extends proximally from the proximal end of the outer tube, and further wherein the inner wire assembly is characterized by a Rockwell Hardness of not less than 50 HRC;

a cutting tip connected to the distal section of the inner wire assembly, wherein at least a portion of the cutting tip extends distal the distal end of the outer tube;

a coupling chuck secured to the proximal section of the inner wire assembly, wherein the coupling chuck is adapted for connection to a drive mechanism of a motor; and a housing maintaining the proximal region of the outer tube and the coupling chuck, the housing being adapted for connection to a motor;

wherein a bearing is established between an outer surface of at least a portion of the inner wire assembly and at least a portion of the inner surface of the outer tube distal the housing upon rotation of the inner wire assembly relative to the outer tube;

and further wherein upon final assembly, the wire assumes a shape of the first curved segment.

64. The instrument of claim 63, wherein an exterior surface of the inner wire assembly is coated with a hardened material.

65. The instrument of claim 64, wherein the hardened material is adapted to provide a dense carbon finish to the inner wire assembly.

66. The instrument of claim 65, wherein the hardened material is diamond-like carbon.

67. The instrument of claim 64, wherein the hardened material includes a material selected from the group consisting of zirconium nitride, chrome, fluorocarbon, titanium nitride, and electroless nickel impregnated with PTFE.

68. The instrument of claim 63, wherein the instrument is characterized by the absence of a ball bearing assembly between the outer tube and the inner wire assembly.

69. The instrument of claim 63, wherein a journal bearing is established between an outer surface of the inner wire assembly and the inner surface of the outer tube upon rotation of the inner wire assembly relative to the outer tube.

70. The instrument of claim 63, wherein the wire is homogenous.

71. The instrument of claim 70, wherein the spring wire is a tool steel.

72. The instrument of claim 70, wherein a rotating journal bearing is established along an entirety of a length of the outer tube distal the housing.

73. The instrument of claim 70, wherein at least a portion of the outer tube distal the housing has a maximum outer diameter of not more than 2 mm.

74. The instrument of claim 70, wherein the wire has an outer diameter of not more than 0.8 mm.

75. The instrument of claim 70, wherein the distal region of the outer tube tapers distally in diameter to the distal end.

76. The instrument of claim 63, further comprising:
a sealing tip connected to the distal region of the outer tube, at least a portion of the sealing tip defining an inner diameter that is less than a diameter of the lumen of the outer tube.

77. The instrument of claim 76, wherein the sealing tip is a ceramic body.

78. The instrument of claim 76, wherein the sealing tip is a tubular body having a proximal portion and a distal portion, the distal portion defining a relaxed state diameter that is less than a diameter of the inner wire assembly, and further wherein upon final assembly, the distal portion of the sealing tip is forced to an expanded state diameter via contact with the inner wire assembly.

79. The instrument of claim 76, wherein the sealing tip is a tubular body shrunk fit to the outer tube and a portion of the inner wire assembly.

80. The instrument of claim 63, further comprising:
a cooling sleeve disposed over at least a portion of the outer tube.

81. A surgical cutting instrument for use with a motor having a drive mechanism, the instrument comprising:
an outer tube defining a first curved segment, a proximal region terminating at a proximal end, a distal region terminating at a distal end, and a lumen extending from the proximal end to the distal end, the lumen being defined by an inner surface of the outer tube, wherein the inner surface is highly polished, exhibiting a surface roughness of not more than 20µ inch RMS;
an inner wire assembly received within the lumen and comprising a wire, the inner wire assembly including a proximal section and distal section, wherein the proximal section extends proximally from the proximal end of the outer tube;
a cutting tip connected to the distal section of the inner wire assembly, wherein at least a portion of the cutting tip extends distal the distal end of the outer tube;
a coupling chuck secured to the proximal section of the inner wire assembly, wherein the coupling chuck is adapted for connection to a drive mechanism of a motor; and
a housing maintaining the proximal region of the outer tube and the coupling chuck, the housing being adapted for connection to a motor;
wherein a bearing is established between an outer surface of at least a portion of the inner wire assembly and at least a portion of the inner surface of the outer tube distal the housing upon rotation of the inner wire assembly relative to the outer tube;
and further wherein upon final assembly, the wire assumes a shape of the first curved segment.

82. The instrument of claim 81, wherein the instrument is characterized by the absence of a ball bearing assembly between the outer tube and the inner wire assembly.

83. The instrument of claim 81, wherein a rotational journal bearing is established between an outer surface of the inner wire assembly and the inner surface of the outer tube upon rotation of the inner wire assembly relative to the outer tube.

84. The instrument of claim 83, further comprising:
a lubricant disposed between the outer surface of the inner wire assembly and the inner surface of the outer tube;
wherein upon rotation of the inner wire assembly relative to the outer tube, the lubricant is adapted to create a hydrodynamic effect.

85. The instrument of claim 81, wherein the wire is homogenous.

86. The instrument of claim 85, wherein the wire is a tool steel.

87. The instrument of claim 85, wherein the journal bearing is established along an entirety of a length of the outer tube distal the housing.

88. The instrument of claim 85, wherein at least a portion of the outer tube distal the housing has a maximum outer diameter of not more than 2 mm.

89. The instrument of claim 85, wherein the wire has an outer diameter of not more than 0.8 mm.

90. The instrument of claim 85, wherein the distal region of the outer tube tapers distally in diameter to the distal end.

91. The instrument of claim 81, further comprising:
a sealing tip connected to the distal region of the outer tube, at least a portion of the sealing tip defining an inner diameter that is less than a diameter of the lumen of the outer tube.

92. The instrument of claim 91, wherein the sealing tip is a ceramic body.

93. The instrument of claim 91, wherein the sealing tip is a tubular body having a proximal portion and a distal portion, the distal portion defining a relaxed state diameter that is less than a diameter of the inner wire assembly, and further wherein upon final assembly, the distal portion of the sealing tip is forced to an expanded state diameter via contact with the inner wire assembly.

94. The instrument of claim 91, wherein the sealing tip is a tubular body shrunk fit to the outer tube and a portion of the inner wire assembly.

95. The instrument of claim 81, further comprising:
a cooling sleeve disposed over at least a portion of the outer tube.

96. A surgical instrument for use with a motor having a drive, mechanism, the instrument comprising:
an outer tube defining a first curved segment, a proximal region terminating at a proximal end, a distal region terminating at a distal end, and a lumen extending from the proximal end to the distal end, the lumen being defined by an inner surface of the outer tube;
an inner wire assembly received within the lumen and comprising a wire, the inner wire assembly including a proximal section and distal section, wherein the proximal section extends proximally from the proximal end of the outer tube;
a cutting tip connected to the distal section of the inner wire assembly, wherein at least a portion of the cutting tip extends distal the distal end of the outer tube;
a coupling chuck secured to the proximal section of the inner wire assembly, wherein the coupling chuck is adapted for connection to a drive mechanism of a motor; and
a housing maintaining the proximal region of the outer tube and the coupling chuck, the housing being adapted for connection to a motor, wherein at least a portion of the outer tube distal the housing has a maximum outer diameter of not more than 2 mm;
wherein a bearing is established between an outer surface of at least a portion of the inner wire assembly and at least a portion of the inner surface of the outer tube distal the housing upon rotation of the inner wire assembly relative to the outer tube;
wherein upon final assembly, the wire assumes a shape of the first curved segment;
and further wherein the instrument is configured to allow rotation of the inner wire assembly relative to the outer tube at a speed of 80,000 RPM without failure of the bearing.

97. The instrument of claim 96, wherein the instrument is characterized by the absence of a ball bearing assembly between the outer tube and the inner wire assembly.

98. The instrument of claim 96, wherein a rotating journal bearing is established between an outer surface of the inner wire assembly and the inner surface of the outer tube upon rotation of the inner wire assembly relative to the outer tube.

99. The instrument of claim 98, further comprising:
a lubricant disposed between the outer surface of the inner wire assembly and the inner surface of the outer tube;
wherein upon rotation of the inner wire assembly relative to the outer tube, the lubricant is adapted to create a hydrodynamic effect.

100. The instrument of claim 96, wherein the wire is homogenous.

101. The instrument of claim 100, wherein the wire is a tool steel.

102. The instrument of claim 100, wherein the journal bearing is established along an entirety of a length of the outer tube distal the housing.

103. The instrument of claim 100, wherein the wire has an outer diameter of not more than 0.8 mm.

104. The instrument of claim 100, wherein an exposed portion of the spring wire extends distally from the distal end of the outer tube, and further wherein the exposed portion has a length of not more than 2.54 mm.

105. The instrument of claim 100, wherein the distal region of the outer tube tapers distally in diameter to the distal end.

106. The instrument of claim 96, further comprising:
a sealing tip connected to the distal region of the outer tube, at least a portion of the sealing tip defining an inner diameter that is less than a diameter of the lumen of the outer tube.

107. The instrument of claim 106, wherein the sealing tip is a ceramic body.

108. The instrument of claim 106, wherein the sealing tip is a tubular body having a proximal portion and a distal portion, the distal portion defining a relaxed state diameter that is less than a diameter of the inner wire assembly, and further wherein upon final assembly, the distal portion of the sealing tip is forced to an expanded state diameter via contact with the inner wire assembly.

109. The instrument of claim 106, wherein the sealing tip is a tubular body shrunk fit to the outer tube and a portion of the inner wire assembly.

110. The instrument of claim 96, further comprising:
a cooling sleeve disposed over at least a portion of the outer tube.

111. A surgical cutting instrument for use with a motor having a drive mechanism, the instrument comprising:
an outer tube defining a first curved segment, a proximal region terminating at a proximal end, a distal region terminating at a distal end, and a lumen extending from the proximal end to the distal end, the lumen being defined by an inner surface of the outer tube;
an inner wire assembly received within the lumen and comprising a wire, the inner wire assembly including a proximal section and distal section, wherein the proximal section extends proximally from the proximal end of the outer tube;
a cutting tip connected to the distal section of the inner wire assembly, wherein at least a portion of the cutting tip extends distal the distal end of the outer tube;
a coupling chuck secured to the proximal section of the inner wire assembly, wherein the coupling chuck is adapted for connection to a drive mechanism of a motor; and
a housing maintaining the proximal region of the outer tube and the coupling chuck, the housing being adapted for connection to a motor;
wherein the outer tube exhibits a stiffness of not less than 15 lbf/inch at the distal end relative to a distal point of interface between the outer tube and the housing;
wherein upon final assembly the wire assumes a shape of the first curved segment;
and further wherein a bearing is established between an outer surface of at least a portion of the inner wire assembly and at least a portion of the inner surface of the outer tube distal the housing upon rotation of the inner wire assembly relative to the outer tube.

112. The instrument of claim 111, wherein the instrument is characterized by the absence of a ball bearing assembly between the outer tube and the inner wire assembly.

113. The instrument of claim 111, wherein a rotating journal bearing is established between an outer surface of the inner wire assembly and the inner surface of the outer tube upon rotation of the inner wire assembly relative to the outer tube.

114. The instrument of claim 111, wherein the wire is homogenous.

115. The instrument of claim 114, wherein the wire is a tool steel.

116. The instrument of claim 114, wherein the journal bearing is established along an entirety of a length of the outer tube distal the housing.

117. The instrument of claim 114, wherein at least a portion of the outer tube distal the housing has a maximum outer diameter of not more than 2 mm.

118. The instrument of claim 114, wherein the distal region of the outer tube tapers distally in diameter to the distal end.

119. The instrument of claim 111, further comprising:
a sealing tip connected to the distal region of the outer tube, at least a portion of the sealing tip defining an inner diameter that is less than a diameter of the lumen of the outer tube.

120. The instrument of claim 119, wherein the sealing tip is a ceramic body.

121. The instrument of claim 119, wherein the sealing tip is a tubular body having a proximal portion and a distal portion, the distal portion defining a relaxed state diameter that is less than a diameter of the inner wire assembly, and further wherein upon final assembly, the distal portion of the sealing tip is forced to an expanded state diameter via contact with the inner wire assembly.

122. The instrument of claim 119, wherein the sealing tip is a tubular body shrunk fit to the outer tube and a portion of the inner wire assembly.

123. The instrument of claim 111, further comprising:
a cooling sleeve disposed over at least a portion of the outer tube.

124. A surgical cutting instrument for use with a motor having a drive mechanism, the instrument comprising:
an outer tube defining a first curved segment, proximal region terminating at a proximal end, a distal region terminating at a distal end, and a lumen extending from the proximal end to the distal end, the lumen being defined by an inner surface of the outer tube, wherein the inner surface is highly polished, exhibiting a surface roughness of not greater than 20μ inch RMS;
an inner wire assembly received within the lumen and comprising a wire, the inner wire assembly including a proximal section and distal section, wherein the proximal section extends proximally from the proximal end of the outer tube, wherein the inner wire assembly is formed to exhibit a fatigue strength of at least 75 Kpsi and a hardness of not less than 50 HRC;

a grease lubricant disposed between the inner surface of the outer tube and an outer surface of the inner wire assembly, the grease lubricant exhibiting a dynamic viscosity of not less than 100 mm²/s at 40° C.;

a cutting tip connected to the distal section of the inner wire assembly, wherein at least a portion of the cutting tip extends distal the distal end of the outer tube;

a coupling chuck secured to the proximal section of the inner wire assembly, wherein the coupling chuck is adapted for connection to a drive mechanism of a motor; and a housing maintaining the proximal region of the outer tube and the coupling chuck, the housing being adapted for connection to a motor, wherein at least a portion of the outer tube distal the housing has a maximum outer diameter of not more than 2 mm;

wherein the outer tube exhibits a stiffness of not less than 15 lbf/inch at the distal end relative to a distal point of interface between the outer tube and the housing;

wherein a hydrodynamic, rotating journal bearing is established between an outer surface of at least a portion of the inner wire assembly and at least a portion of the inner surface of the outer tube distal the housing upon rotation of the inner wire assembly relative to the outer tube;

and further wherein upon final assembly, the wire assumes a shape of the first curved segment;

and further wherein the instrument is configured to allow rotation of the inner wire assembly relative to the outer tube at a speed of 80,000 RPM without failure of the journal bearing.

125. The instrument of claim 124, wherein the instrument is characterized by the absence of a ball bearing assembly between the outer tube and the inner wire assembly.

126. The instrument of claim 124, wherein the wire is homogenous.

127. The instrument of claim 126, wherein the wire is formed of a tool steel material.

128. The instrument of claim 124, further comprising:
a sealing tip connected to the distal region of the outer tube, at least a portion of the sealing tip defining an inner diameter that is less than a diameter of the lumen of the outer tube.

129. The instrument of claim 128, wherein the sealing tip is a ceramic body.

130. The instrument of claim 128, wherein the sealing tip is a tubular body having a proximal portion and a distal portion, the distal portion defining a relaxed state diameter that is less than a diameter of the inner wire assembly, and further wherein upon final assembly, the distal portion of the sealing tip is forced to an expanded state diameter via contact with the inner wire assembly.

131. The instrument of claim 128, wherein the sealing tip is a tubular body shrunk fit to the outer tube and a portion of the inner wire assembly.

132. The instrument of claim 124, further comprising:
a cooling sleeve disposed over at least a portion of the outer tube.

* * * * *